(12) United States Patent
Zhang et al.

(10) Patent No.: US 11,564,661 B2
(45) Date of Patent: Jan. 31, 2023

(54) METHOD FOR OPTIMIZING ULTRASONIC IMAGING SYSTEM PARAMETER BASED ON DEEP LEARNING

(71) Applicant: Chison Medical Technologies Co., LTD., Wuxi (CN)

(72) Inventors: Zhiwei Zhang, Wuxi (CN); Mingchang Zhao, Wuxi (CN); Jian Lu, Wuxi (CN)

(73) Assignee: Chison Medical Technologies Co., LTD., Wuxi (CN)

( * ) Notice: Subject to any disclaimer, the term of this patent is extended or adjusted under 35 U.S.C. 154(b) by 307 days.

(21) Appl. No.: 16/766,643

(22) PCT Filed: Jun. 29, 2018

(86) PCT No.: PCT/CN2018/093561
§ 371 (c)(1),
(2) Date: May 22, 2020

(87) PCT Pub. No.: WO2019/100718
PCT Pub. Date: May 31, 2019

(65) Prior Publication Data
US 2020/0345330 A1    Nov. 5, 2020

(30) Foreign Application Priority Data

Nov. 24, 2017  (CN) .......................... 201711224993.0

(51) Int. Cl.
*G06T 7/00* (2017.01)
*A61B 8/08* (2006.01)
(Continued)

(52) U.S. Cl.
CPC ......... *A61B 8/5223* (2013.01); *G06N 3/0454* (2013.01); *G06N 3/08* (2013.01);
(Continued)

(58) Field of Classification Search
CPC ......... A61B 8/5223; A61B 8/54; A61B 8/585; G06N 3/0454; G06N 3/08; G06N 3/0445;
(Continued)

(56) References Cited

U.S. PATENT DOCUMENTS

2003/0045797 A1   3/2003   Christopher et al.
2010/0189329 A1   7/2010   Mo et al.
(Continued)

FOREIGN PATENT DOCUMENTS

CN    102184330 A    9/2011
CN    104572940 A    4/2015
(Continued)

OTHER PUBLICATIONS

Extended European Search Report dated Aug. 4, 2021, in corresponding European application No. 18880759.8, 11 pages.

*Primary Examiner* — Siamak Harandi
(74) *Attorney, Agent, or Firm* — Finnegan, Henderson, Farabow, Garrett & Dunner LLP

(57) ABSTRACT

A method for optimizing an ultrasonic imaging system parameter based on deep learning, comprising the following steps: step 1: collecting samples for training neural networks, the samples comprising ultrasound image samples i, and a corresponding ultrasonic imaging system parameter vector sample p used by an ultrasonic imaging system when the ultrasonic image samples are collected; step 2: establishing a neural network model and training the neural networks to convergence by using the samples collected=in step 1, so as to obtain a trained neural network system onn; and step 3: taking the original ultrasonic imaging system parameter vector p or the original ultrasonic image as an input to be input into the neural network system onn trained in step 2, at this moment, a parameter obtained from an output end of onn being an optimized ultrasonic imaging system parameter vector ep=onn(p). By means of the
(Continued)

Parameter vector p of an ultrasound imaging system; and ultrasound image i generated under the current imaging  Pre-trained neural network system  Optimized ultrasound imaging system parameter vector ep=onn(p,i)

method, the purpose of improving the ultrasonic image quality is realized by optimizing the ultrasonic imaging system parameter.

7 Claims, 28 Drawing Sheets

(51) Int. Cl.
  *G16H 30/40* (2018.01)
  *G06N 3/04* (2006.01)
  *G06N 3/08* (2006.01)
(52) U.S. Cl.
  CPC ........... *G06T 7/0012* (2013.01); *G16H 30/40* (2018.01); *G06T 2207/10132* (2013.01); *G06T 2207/20081* (2013.01); *G06T 2207/20084* (2013.01)

(58) Field of Classification Search
  CPC .... G06N 3/0472; G06N 3/088; G06T 7/0012; G06T 2207/10132; G06T 2207/20081; G06T 2207/20084; G16H 30/40
  See application file for complete search history.

(56) References Cited

U.S. PATENT DOCUMENTS

2017/0143312 A1    5/2017  Hedlund et al.
2019/0018933 A1*   1/2019  Oono ..................... G06N 7/08

FOREIGN PATENT DOCUMENTS

CN         105574820 A      5/2016
WO    WO 2017/122785 A1    7/2017

* cited by examiner

Presets

Image acquisition parameters
- Transmission power
- Transmission frequency
- Receiving frequency
- Beam density
- Penetration depth
- Total gain
- Time gain compensation
- Focal position
- Pulse repetition frequency

Display parameters
- Dynamic range
- Image resolution
- Contrast
- Zoom in and zoom out ratios
- Gamma correction
- Gray mapping
- Color mapping

Signal processing parameters
- Edge enhancement
- Smoothing
- Noise filtering
- Wall filtering
- Linear correlation
- Frame correlation
- Interpolation algorithm

FIG. 28

METHOD FOR OPTIMIZING ULTRASONIC IMAGING SYSTEM PARAMETER BASED ON DEEP LEARNING

TECHNICAL FIELD

The present disclosure relates to a medical ultrasound imaging system, and more particularly, relates to a method for optimizing parameters of the ultrasound imaging system.

BACKGROUND

Ultrasound imaging has been widely used in clinical practice because the ultrasound imaging has advantages of no invasion, low price, fast imaging, and the like. However, there are many parameters of an image due to the physical characteristics of ultrasound imaging. To obtain a desired ultrasound image, many parameters need to be adjusted, and it is relatively cumbersome for a user to adjust the parameters.

At present, most of ultrasonic diagnostic apparatuses provide presets for setting presets of various imaging parameters. The preset is a set that contains all adjustable imaging parameters. Commonly used imaging parameters can be roughly divided into three categories: image acquisition parameters, display parameters, and signal processing parameters. The image acquisition parameters mainly control front-end modules, such as a transmission circuit, a receiving circuit, a transducer, and a beam combiner. These parameters can control the brightness, contrast, resolution, penetration rate, and other properties of an image. For example, when the image is relatively dark, a gain parameter may be properly increased to make the entire image become brighter. If the brightness of ranges on the image needs to be precisely controlled, a plurality of time compensation gains can be controlled to control the brightness of images in different ranges. The display parameters mainly control back-end modules, such as an image processor and a display. These parameters mainly affect the brightness, contrast, zoom in and zoom out ratios, pseudo-color displaying, and the like of final image displaying. The signal processing parameters mainly control a signal processor module and an image processor module, and are configured to perform various filtering processing on a beam combined signal. Values of these parameters have relatively high impact on an image effect.

With the development of social technologies, a deep learning technology has made some progresses in other fields. However, in the field of medical ultrasound, the deep learning technology still has some defects in the field of medical devices due to the complexity of an ultrasound system and still cannot adjust the current presets fast, accurately and intelligently according to a current image.

SUMMARY

The objective of the present disclosure is to overcome the conventional shortcomings, and provides a deep learning-based method for optimizing parameters for an ultrasound imaging system, which may be applied to ultrasound imaging. In the present disclosure, a mapping relation is established between the quality of an image and parameters of the ultrasound imaging system by training an artificial neural network, thereby achieving the objective of improving the quality of an ultrasound image by optimizing the parameters of the ultrasound imaging system. The technical solution adopted by the present disclosure is as follows.

A deep learning-based method for optimizing parameters of an ultrasound imaging system includes the following steps:

step 1: collecting samples for training a neural network, wherein the samples include ultrasound image samples I and corresponding ultrasound imaging system parameter vector samples P used by an ultrasound imaging system during collection of the ultrasound image samples;

step 2: building a neural network model, training a neural network by using the samples collected in Step 1 till the neural network is converged, so as to obtain a trained neural network system onn; and step 3: inputting an original ultrasound imaging system parameter vector p or an original ultrasound image as an input into the neural network system onn trained in step 2, wherein at the moment, a parameter obtained from the output end of the "onn" is an optimized ultrasound imaging system parameter vector ep=onn(p).

The present disclosure has the advantages that the present disclosure optimizes the ultrasound imaging system parameters by means of deep learning, and establishes the mapping relation between the quality of the image and the ultrasound imaging system parameters, thereby achieving the objective of improving the quality of the image by optimizing the ultrasound imaging system parameters.

BRIEF DESCRIPTION OF THE DRAWINGS

FIG. 28 is a schematic diagram of preset-related parameters of the embodiments of the present disclosure.

DETAILED DESCRIPTION

The present disclosure is further described below in combination with specific drawings and embodiments.

Figure 1:
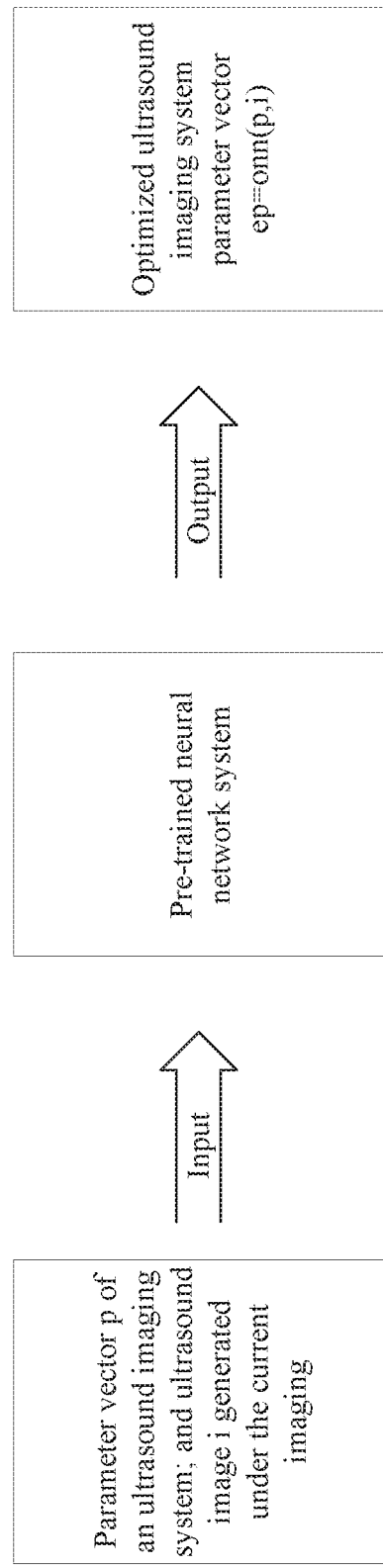
FIG. 1 is a system block diagram of the present disclosure.
Figure 2:
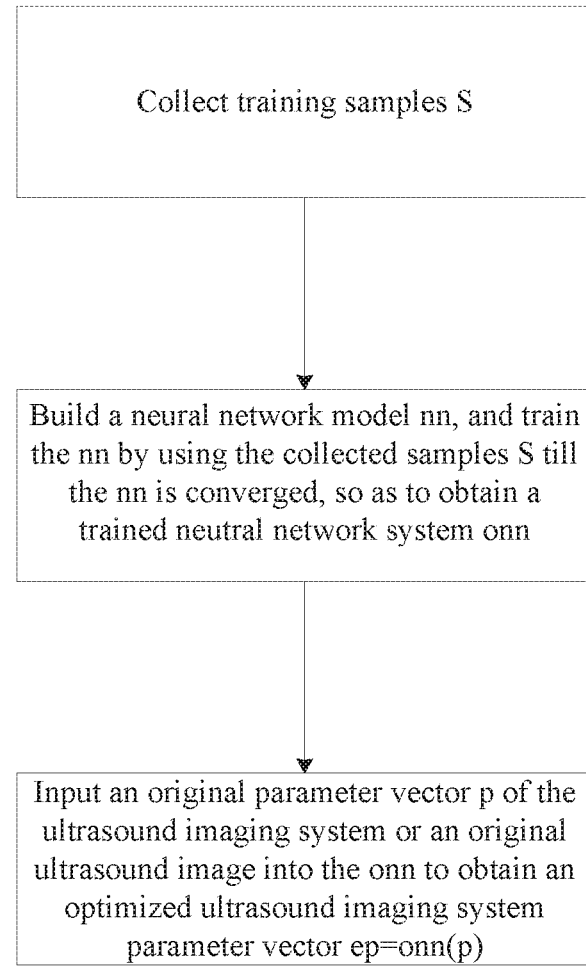
FIG. 2 is a flowchart of general implementation of the present disclosure.

The system block diagram of the technical solution of the present disclosure is as shown in FIG. 1, and FIG. 2 illustrates an implementation flowchart of this technical solution.

A deep learning-based method for optimizing parameters of the ultrasound imaging system can include the following steps.

In step 1, N groups of samples for training a neural network can be collected. The samples include, but not limited to, ultrasound image samples I and corresponding parameter vector samples P of an ultrasound imaging system used by the ultrasound imaging system during collection of the ultrasound image samples.

In step 2, a neural network model can be created and trained till the neural network is converged by using the samples collected in step 1, so as to obtain a trained neural network system "onn."

In step 3, an original parameter vector p of the ultrasound imaging system or an original ultrasound image can be input into the neural network system "onn" trained in step 2 as inputs. A parameter obtained from the output end of "onn" is an optimized ultrasound imaging system parameter vector ep=onn(p) at the moment.

Embodiment 1: specifically, this technical solution is divided into a training stage and an application stage which are performed in sequence. Steps of each of the stages are as follows.

A training stage can include steps as below.

In step 101, presets of the parameters of the ultrasound imaging system are randomly selected from ultrasound apparatus. And one ultrasound image can be acquired under the preset condition every time when one preset is selected. The ultrasound image is stored, and the preset parameters used by the acquisition of the ultrasound image is recorded at the same time, so as to respectively obtain an image sample set OI (e.g., including 1000 images) and a preset parameter sample set OP (e.g., including 1000 groups of preset parameters).

In step 102, an optimized image sample set EI (e.g., including 1000 images, each of which is consistent with each image content in the OI, but is higher in quality) corresponding to the OI is obtained.

Figure 3:
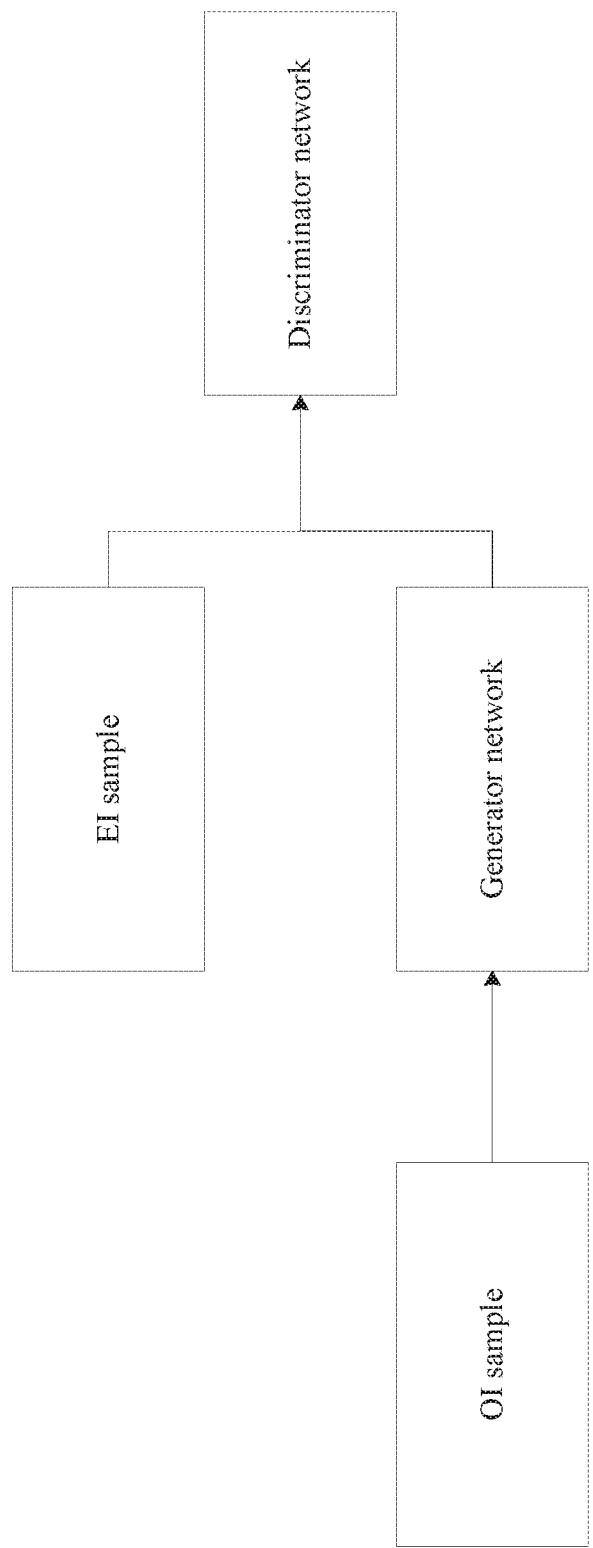
FIG. 3 is a schematic diagram of training a DCGAN (Deep Convolutional Generation Adversarial Network) in Embodiment I of the present disclosure.

In step 103, a Deep Convolutional Generation Adversarial Network (DCGAN) as shown in FIG. 3 is trained by using the OI and the EI till a generator network of the DCGAN may output a corresponding optimized image under the condition of a specified original ultrasound image, so as to obtain a trained DCGAN.

The DCGAN includes the generator network and a discriminator network. An OI sample is input into the generator network, and an image corresponding to the OI sample can be generated through the generator network. Then the discriminator network performs consistency comparison on the image generated by the generator network and a corresponding EI sample.

Figure 4:
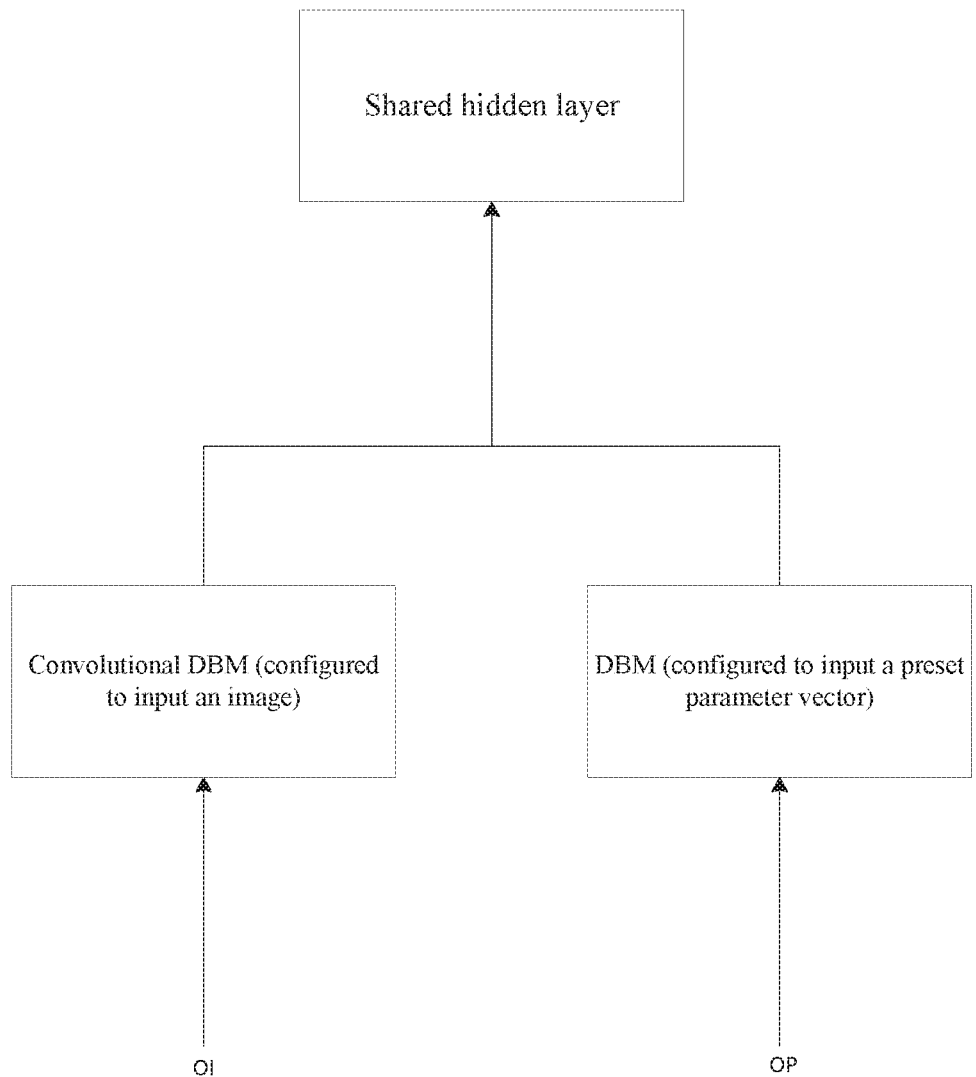
FIG. 4 is a schematic diagram of training a DBM (Depth Boltzmann Machine) in Embodiment I of the present disclosure.

In step 104, a multi-mode Depth Boltzmann Machine (DBM) as shown in FIG. 4 is trained by using the OP and the OI till the DBM is converged, so as to obtain a trained multi-mode DBM.

The multi-mode DBM includes a convolutional DBM, a common DBM, and a shared hidden layer for connecting the convolutional DBM to the common DBM. The OI is input into the convolutional DBM, and the OP is input into the common DBM. The shared hidden layer establishes a connection between OI information and OP information;

An application stage can include steps as below.

Figure 5:
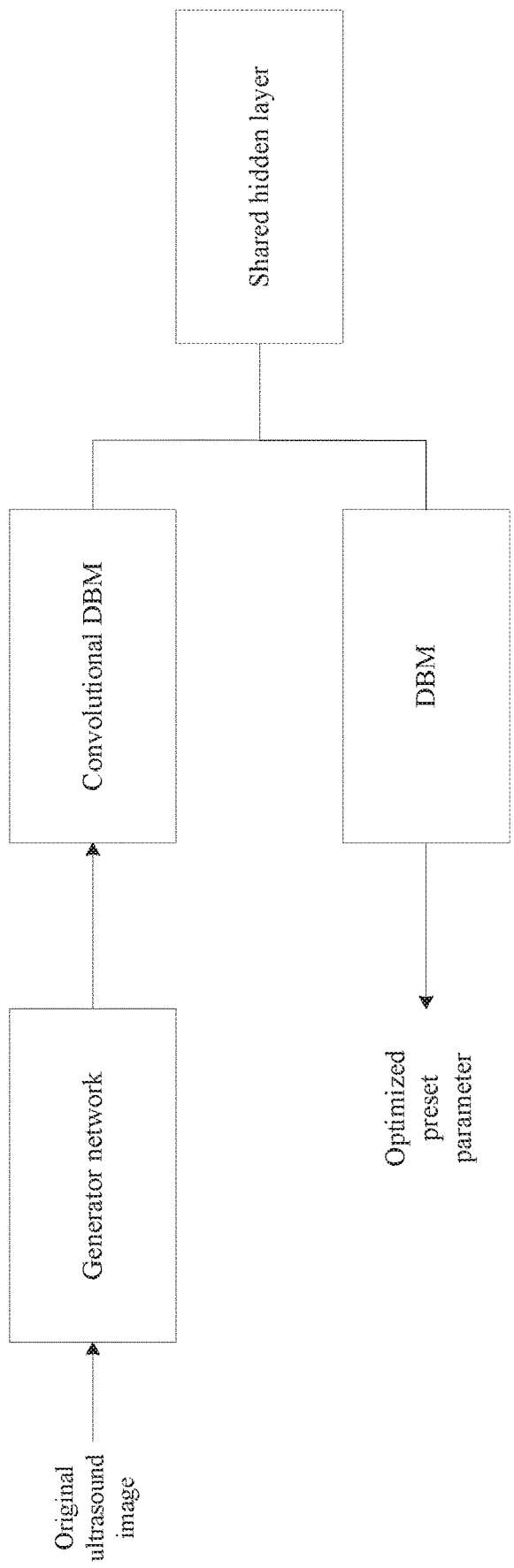
FIG. 5 is a schematic diagram of a neural network system in an application stage in Embodiment I of the present disclosure.

In step a101, an artificial neural network system as shown in FIG. 5 is formed by the generator network part of the DCGAN trained in step 103 in the training stage and the multi-mode DBM trained in step 104 in the training stage, wherein the output end of the generator network is connected with the input end of the convolutional DBM.

In step a102, an original ultrasound image is input into the input end (i.e., an image input end) of the generator network in FIG. 5, and the parameter vector end of the common DBM outputs an optimized parameter vector (i.e., an optimized preset parameter vector) of the ultrasound imaging system.

Specifically, the ultrasonic imaging system parameter set of step 101 includes: a transmission power p1, a transmission frequency p2, a receiving frequency p3, a beam density p4, a penetration depth p5, a total gain p6, time gain compensation p7, a focus position p8, a pulse repetition frequency p9, a dynamic range p10, an image resolution p11, edge enhancement p12, and the like. And p1 to p12 represent ultrasound images obtained by the respective parameters at the moment under the preset set.

Embodiment 2: this technical solution is specifically divided into a training stage and an application stage which are performed in sequence. Steps of each of the stages are as follows.

A training stage can include steps as below.

In step 201, presets of parameters of the ultrasound imaging system are randomly selected from an ultrasound apparatus, and one ultrasound image is acquired under the preset condition every time when one preset is selected. The ultrasound image is stored, and the preset parameter used by acquisition of the ultrasound image is recorded at the same time, so as to respectively obtain an image sample set OI (e.g., including 2000 images) and a preset parameter sample set OP (e.g., including 2000 groups of preset parameters).

In step 202, an optimized image sample set EI (e.g., including 2000 images, each of which is consistent with each image content in the OI, but is higher in quality) corresponding to the OI is obtained.

Figure 6:
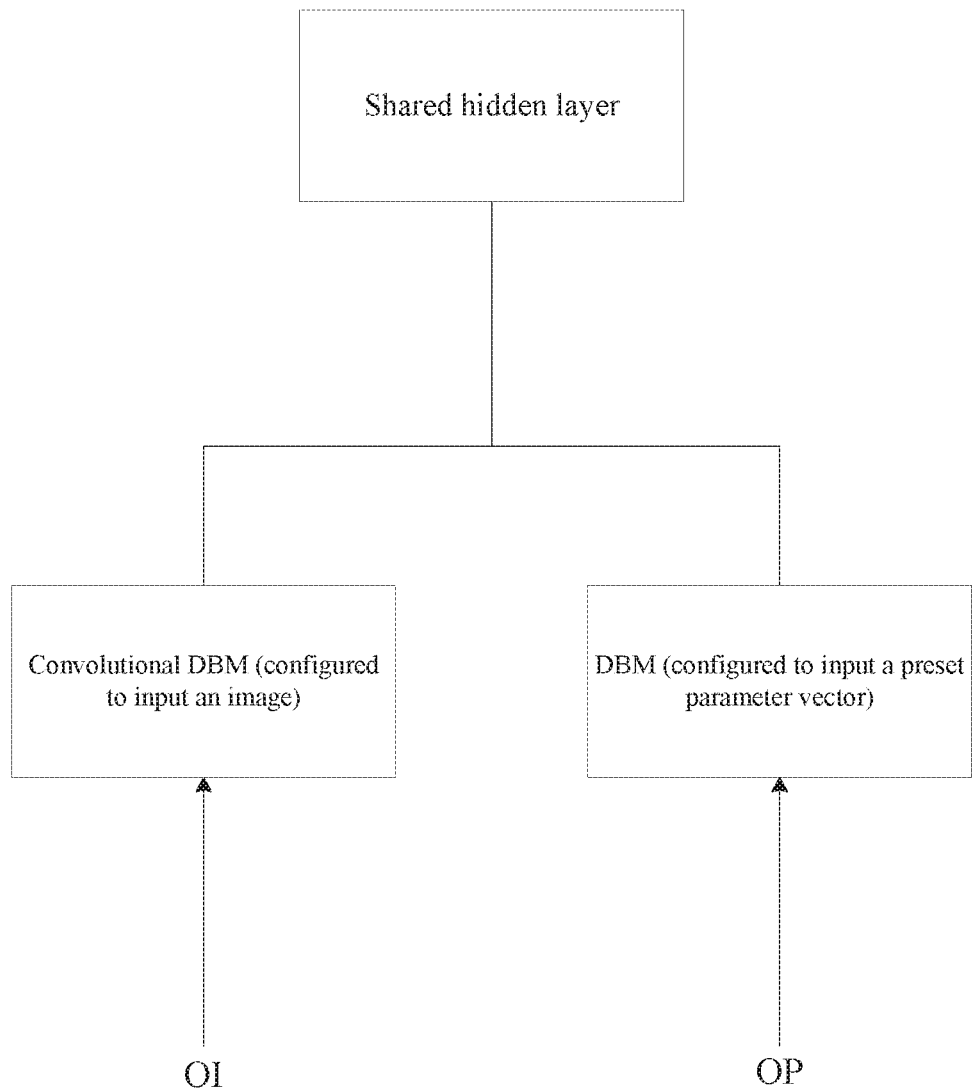
FIG. 6 is a schematic diagram of training a multi-mode DBM in Embodiment II of the present disclosure.

In step 203, a multi-mode Depth Boltzmann Machine (DBM) as shown in FIG. 6 is trained by using the sample set OI and the sample set OP till the DBM is converged, so as to obtain a trained multi-mode DBM.

The multi-mode DBM includes a convolutional DBM, a common DBM, and a shared hidden layer for connecting the convolutional DBM to the common DBM. the OI is input into the convolutional DBM, and the OP is input into the common DBM. The shared hidden layer establishes a connection between OI information and OP information.

Figure 7:
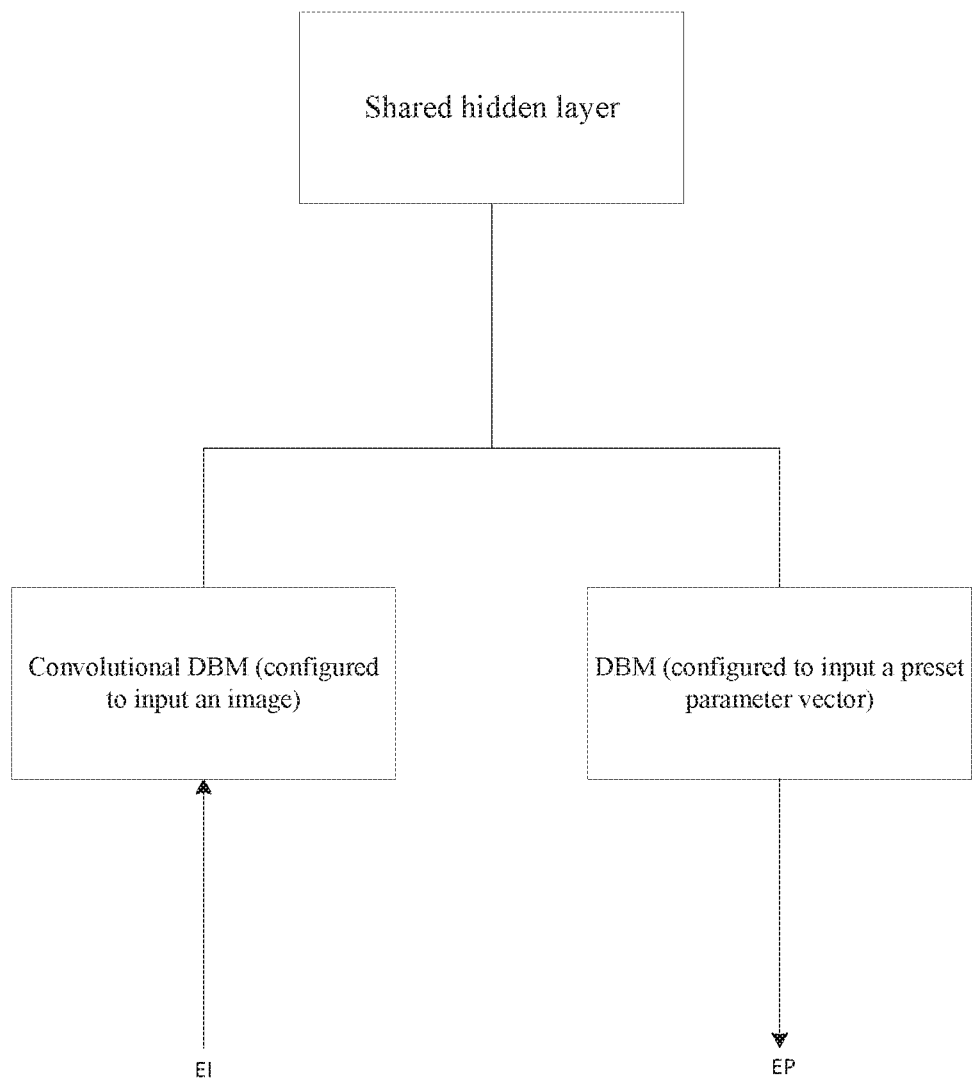
FIG. 7 is a schematic diagram of obtaining an optimized preset parameter vector EP in Embodiment II of the present disclosure.
Figure 8:
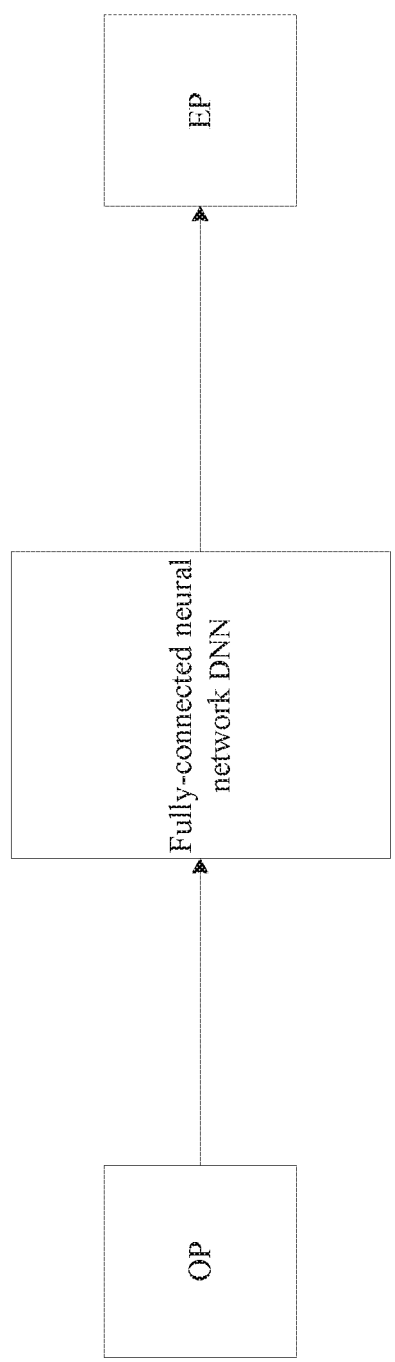
FIG. 8 is a schematic diagram of training a fully connected neural network in Embodiment II of the present disclosure.

In step 204, the sample set EI is input to the input end of the convolutional DBM of the trained multi-mode DBM in step 203. At this moment, a result output by the multi-mode DBM from the preset parameter end (i.e., the parameter vector end of the common DBM) is a corresponding optimized preset parameter vector EP, and the process is as shown in FIG. 7;

In step 205, a fully-connected neural network DNN as shown in FIG. 8 is trained by using the OP as an input and using the EP as an output.

An application stage can include steps as below.

In step a201, a preset parameter vector is input to the input end of the trained fully-connected neural network DNN obtained in step 205 in the training stage. At this moment, a vector obtained at the output end is an optimized parameter vector (i.e., the optimized preset parameter vector) of the ultrasound imaging system.

Embodiment 3: this technical solution is specifically divided into a training stage and an application stage which are performed in sequence. Steps of each of the stages are as follows.

A training stage can include steps as below.

In step 301, presets of parameters of the ultrasound imaging system are randomly selected from an ultrasound apparatus, and one ultrasound image is acquired under the preset condition every time when one preset is selected. The ultrasound image is stored, and the preset parameter used by acquisition of the ultrasound image is recorded at the same time, so as to respectively obtain an image sample set OI (e.g., including 2000 images) and a preset parameter sample set OP (e.g., including 2000 groups of preset parameters).

In step 302, an optimized image sample set EI (e.g., including 2000 images, each of which is consistent with each image content in the OI, but is higher in quality) corresponding to the OI is obtained.

Figure 9:
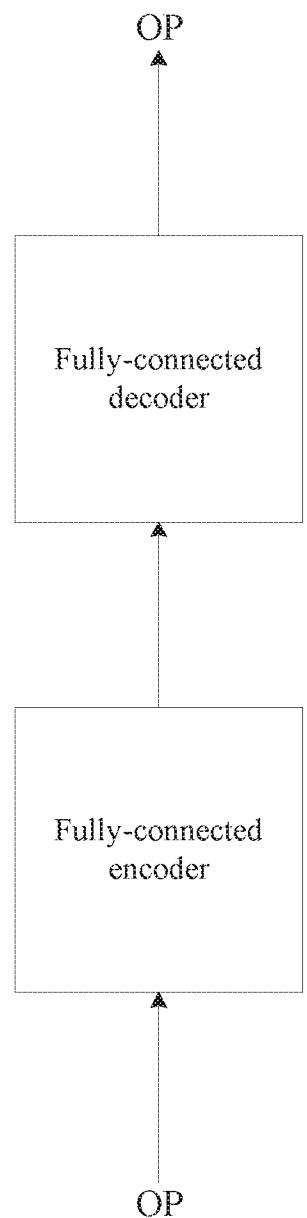
FIG. 9 is a schematic diagram of training a fully connected automatic encoder in Embodiment III of the present disclosure.

In step 303, a fully-connected automatic encoder DNN-AutoEncoder is trained by using the preset parameter sample set OP, as shown in FIG. 9.

The fully-connected automatic encoder includes a fully-connected encoder and a fully-connected decoder, which are cascaded with each other. The fully-connected encoder is configured to compress high-dimension input information to a low-dimension space, and the fully-connected decoder is configured to convert the compressed low-dimension space information into the original high-dimension space.

Figure 10:
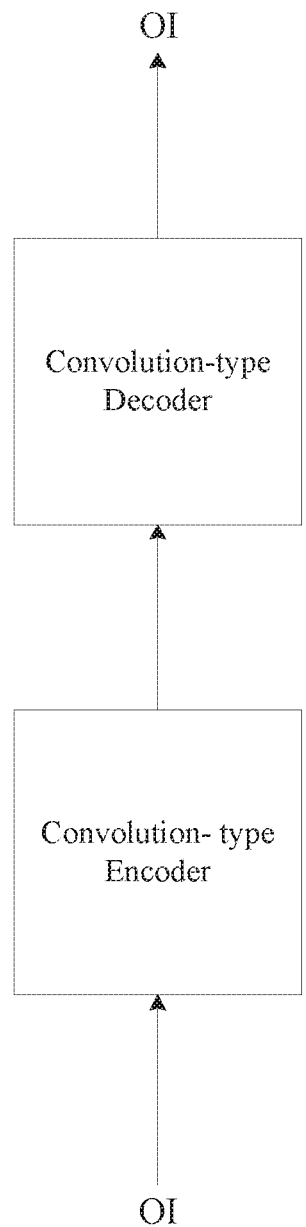
FIG. 10 is a schematic diagram of training a convolution type automatic encoder in Embodiment III of the present disclosure.

In step 304, a convolution type automatic encoder CNN-AutoEncoder is trained by using the image sample set OI, as shown in FIG. 10.

The convolution-type automatic encoder includes a convolution-type encoder and a convolution-type decoder, which are cascaded with each other. The convolution-type encoder is configured to compress high-dimension input information to a low-dimension space, and the convolution-type decoder is configured to convert the compressed low-dimension space information into the original high-dimension space.

Figure 11:
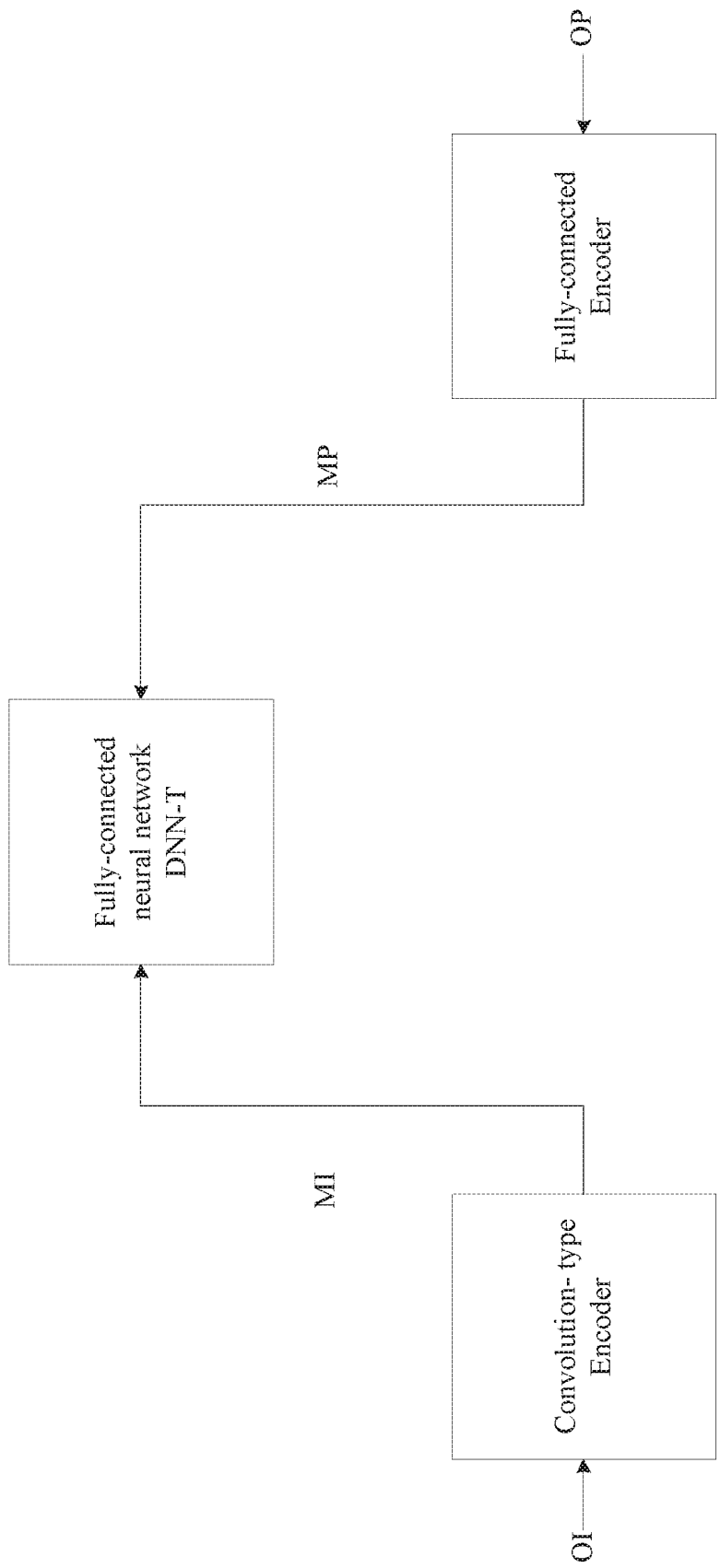
FIG. 11 is a schematic diagram of training a fully connected neural network DNN-T in Embodiment III of the present disclosure.
Figure 12:
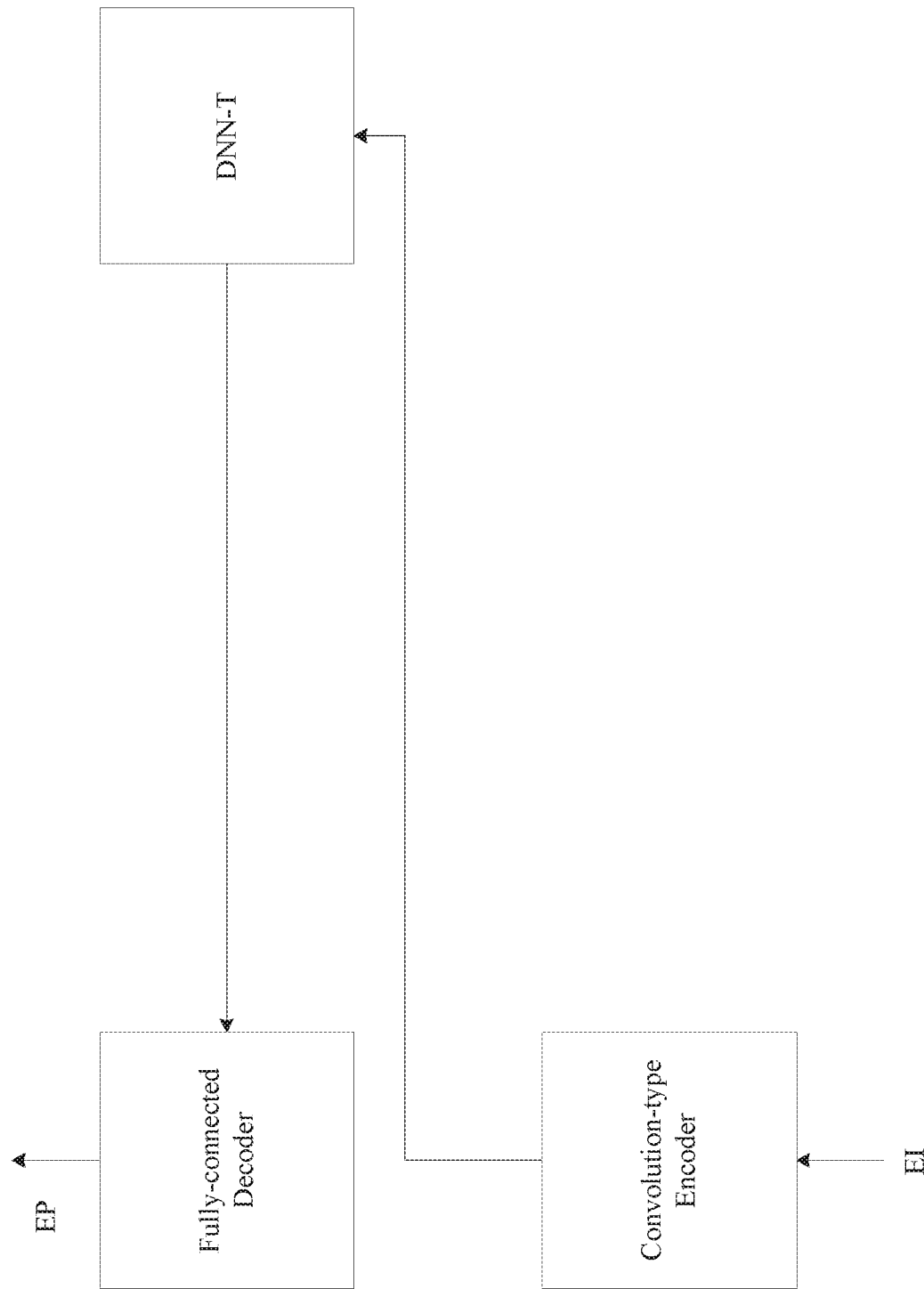
FIG. 12 is a schematic diagram of obtaining an optimized preset parameter sample set EP through a neural network system in Embodiment III of the present disclosure.

In step 305, the OI is input into the convolution-type encoder of the CNN-AutoEncoder trained in step 304 to obtain an output MI, and the OP is input into the fully-connected encoder of the DNN-AutoEncoder in step 303 to obtain an output MP. A fully-connected neural network DNN-T is trained by using the MI as an input and using the MP as an output, as shown in FIG. 11;

In step 306, a neural network system as shown in FIG. 12 is formed by the convolution-type encoder part of the CNN-AutoEncoder, the fully-connected decoder part of the DNN-AutoEncoder, and the DNN-T.

The convolution-type encoder part of the CNN-AutoEncoder is connected with the DNN-T, and the DNN-T is connected with the fully-connected decoder part of the DNN-AutoEncoder.

The sample set EI is input to the convolution-type encoder end of the neural network system CNN-AutoEncoder, and an optimized preset parameter sample set EP is obtained at the output end of the fully-connected decoder of the neural network system DNN-AutoEncoder.

Figure 13:
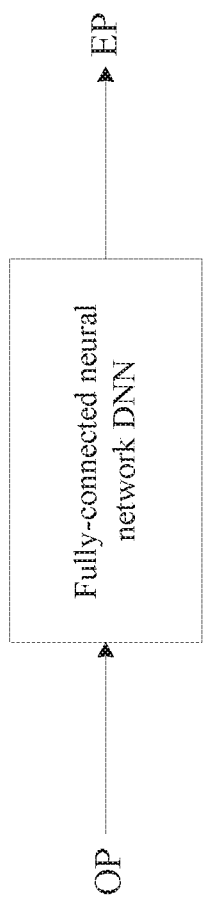
FIG. 13 is a schematic diagram of training a fully connected neural network DNN in Embodiment III of the present disclosure.

In step 307, a fully-connected neural network DNN as shown in FIG. 13 is trained by using the preset parameter sample set OP obtained in step 301 and the optimized preset parameter sample set EP obtained in step 306 till the network is converged;

An application stage can include steps as below.

In step a301, a preset parameter vector is input to the DNN obtained in step 307 in the training stage, and an optimized parameter vector of the ultrasound imaging system is obtained at the output end.

Embodiment 4: this technical solution is specifically divided into a training stage and an application stage which are performed in sequence. Steps of each of the stages are as follows.

A training stage can include steps as below.

In step 401, presets of parameters of the ultrasound imaging system are randomly selected from an ultrasound apparatus, and one ultrasound image is acquired under the preset condition every time when one preset is selected. The ultrasound image is stored, and the preset parameter used by acquisition of the ultrasound image is recorded at the same time, so as to respectively obtain an image sample set OI (e.g., including 2000 images) and a preset parameter sample set OP (e.g., including 2000 groups of preset parameters);

In step 402, an optimized image sample set EI (e.g., including 2000 images, each of which is consistent with each image content in the OI, but is higher in quality) corresponding to the OI is obtained.

Figure 14:
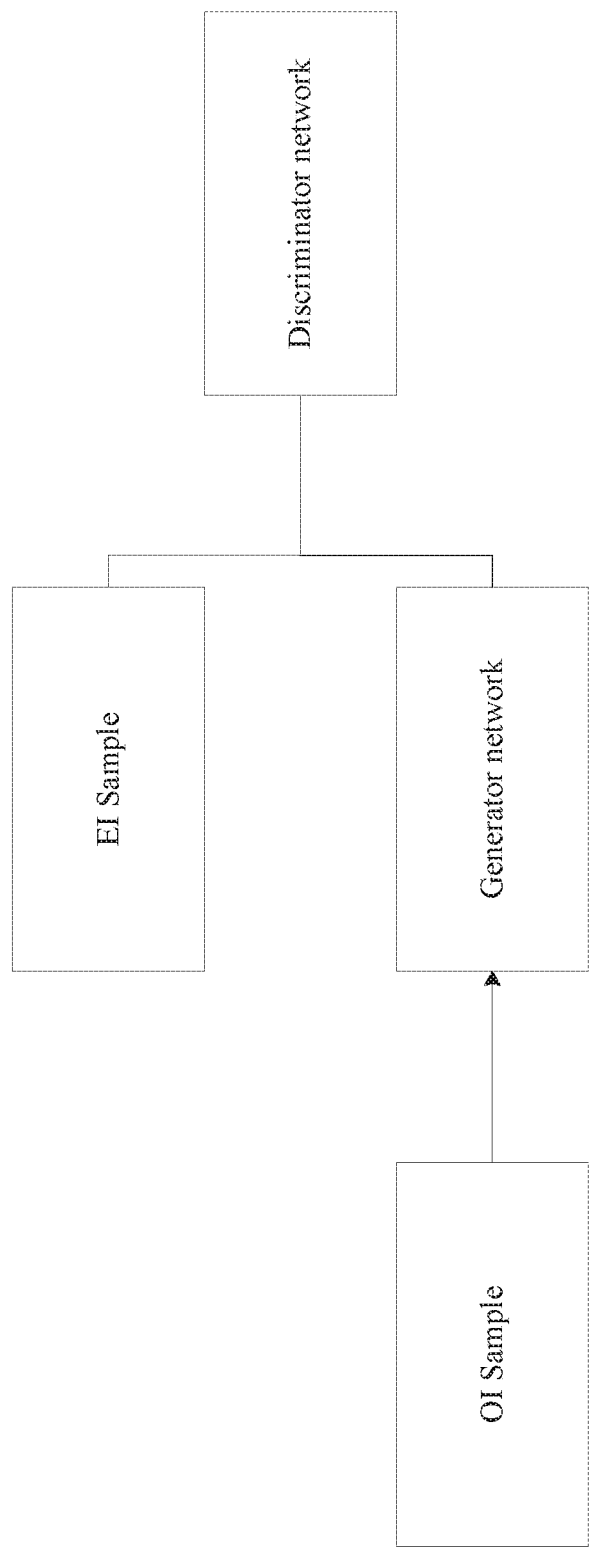
FIG. 14 is a schematic diagram of training a DCGAN in Embodiment IV of the present disclosure.

In step 403, a DCGAN as shown in FIG. 14 is trained by using the sample sets OI and EI till a generator network of the DCGAN may output a corresponding optimized image under the condition of inputting an original ultrasound image, so as to obtain a trained DCGAN.

The DCGAN includes a generator network and a discriminator network. An OI sample is input into the generator network, and an image corresponding to the OI sample is generated through the generator network. Then the discriminator network performs consistency comparison on the image generated by the generator network and a corresponding EI sample.

Figure 15:
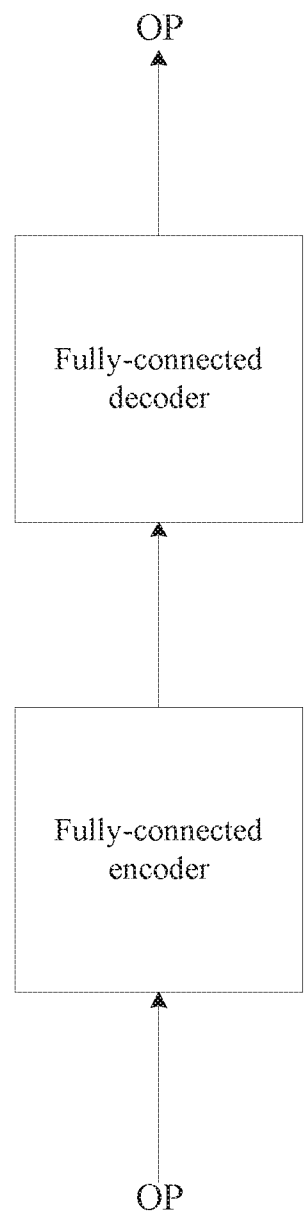
FIG. 15 is a schematic diagram of training a fully connected automatic encoder in Embodiment IV of the present disclosure.

In step 404, a fully-connected automatic encoder DNN-AutoEncoder is trained by using the preset parameter sample set OP, as shown in FIG. 15;

The fully-connected automatic encoder includes a fully-connected encoder and a fully-connected decoder, which are cascaded with each other. The fully-connected encoder is configured to compress high-dimension input information to a low-dimension space, and the fully-connected decoder is configured to convert the compressed low-dimension space information into the original high-dimension space.

Figure 16:
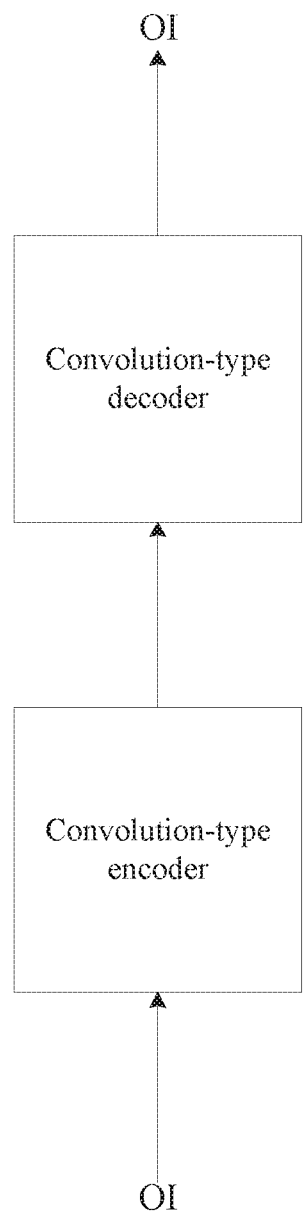
FIG. 16 is a schematic diagram of training a convolution type automatic encoder in Embodiment IV of the present disclosure.

I step 405, a convolution-type automatic encoder CNN-AutoEncoder is trained by using the image sample set OI, as shown in FIG. 16;

The convolution-type automatic encoder includes a convolution-type encoder and a convolution-type decoder, which are cascaded with each other. The convolution-type encoder is configured to compress high-dimension input information to a low-dimension space, and the convolution-type decoder is configured to convert the compressed low-dimension space information into the original high-dimension space.

Figure 17:
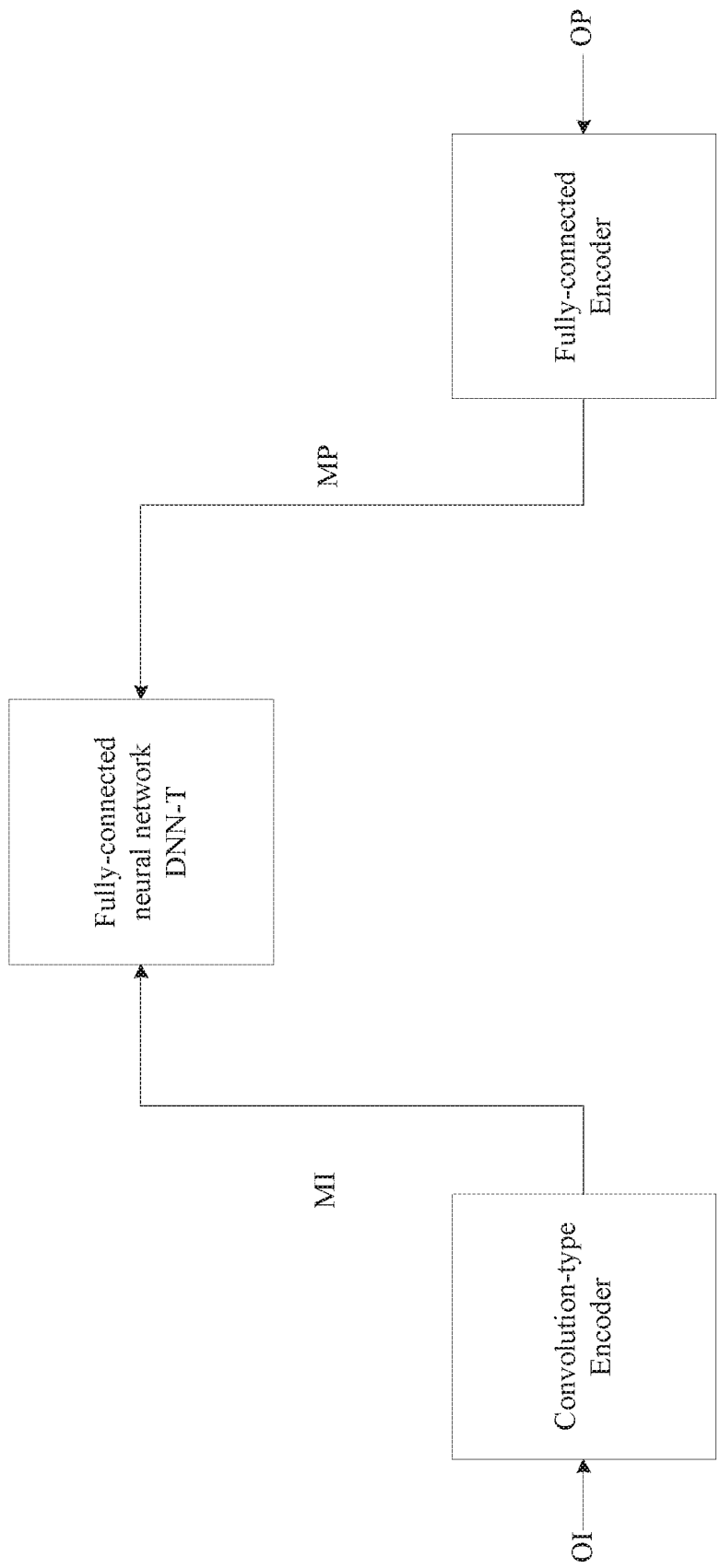
FIG. 17 is a schematic diagram of training a fully connected neural network DNN-T in Embodiment IV of the present disclosure.

In step 406, the OI is input into the convolution-type encoder of the CNN-AutoEncoder trained in step 405 to obtain an output MI, and the OP is input into the fully-connected encoder of the DNN-AutoEncoder in step 404 to obtain an output MP. The fully-connected neural network DNN-T is trained by using the MI as an input and using the MP as an output, as shown in FIG. 17.

An application stage can include steps as below.

Figure 18:
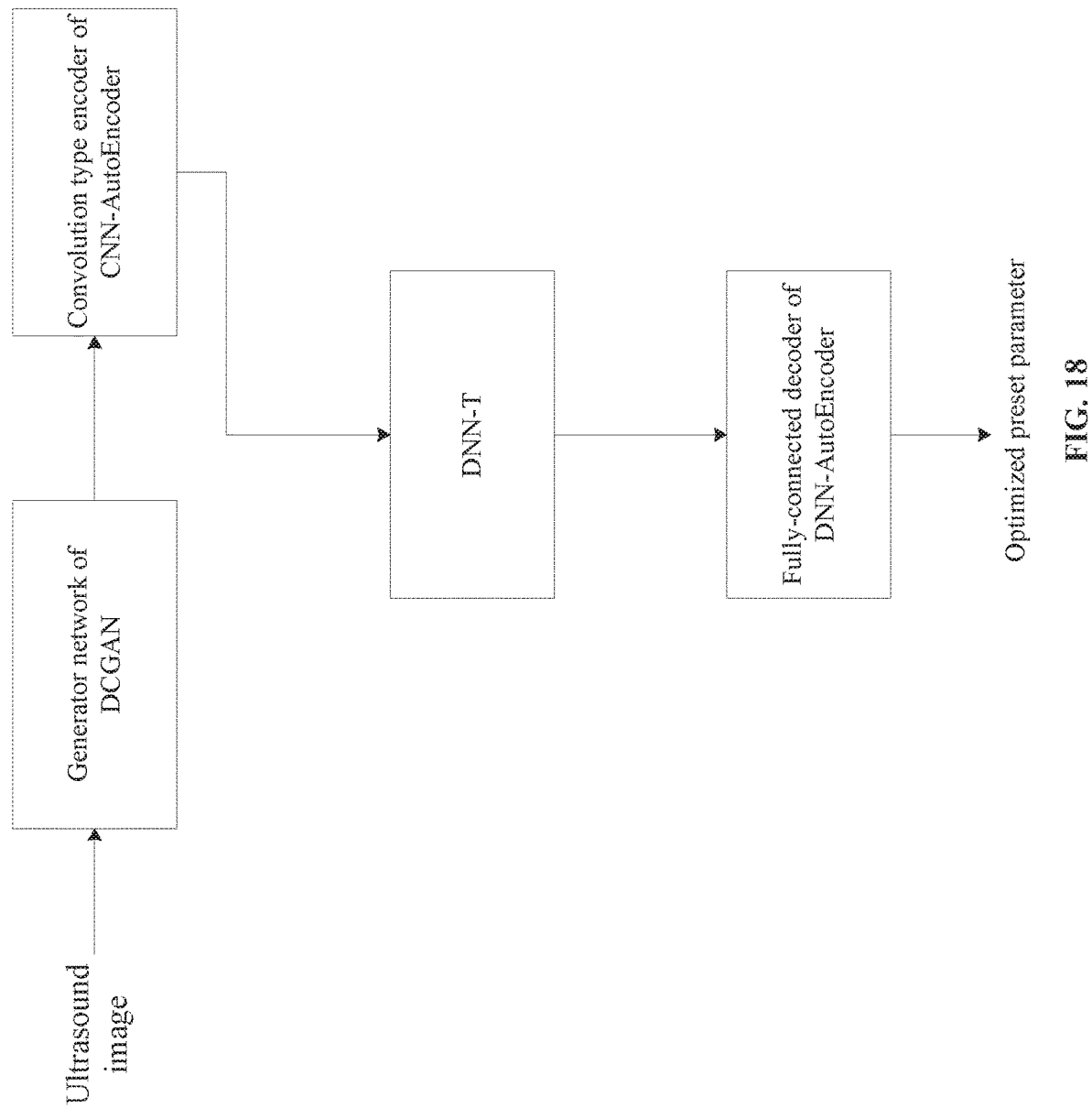
FIG. 18 is a schematic diagram of a combined neural network system in Embodiment IV of the present disclosure.

In step a401, a neural network system as shown in FIG. 18 is formed by the generator network of the DCGAN trained in step 403, the fully-connected decoder of the DNN-AutoEncoder trained in step 404 and the convolution-type encoder of the CNN-AutoEncoder trained in step 405.

The generator network of the DCGAN is connected with the convolution type encoder of the CNN-AutoEncoder. The convolution type encoder of the CNN-AutoEncoder is connected with the DNN-T. The DNN-T is connected with the fully-connected encoder of the DNN-AutoEncoder.

In step a402, an original ultrasound image is input to the neural network system as shown in FIG. 18. And at this moment, an output of the neural network system is an optimized parameter vector of the ultrasound imaging system (i.e., an optimized preset parameter vector).

Embodiment 5: this technical solution is specifically divided into a training stage and an application stage which are performed in sequence. Steps of each of the stages are as follows.

A training stage can include steps as below.

In step 501, presets of parameters of the ultrasound imaging system are randomly selected from an ultrasound apparatus, and one ultrasound image is acquired under the preset condition every time when one preset is selected. The ultrasound image is stored, and the preset parameter used by acquisition of the ultrasound image is recorded at the same time, so as to respectively obtain an image sample set OI (e.g., including 2000 images) and a preset parameter sample set OP (e.g., including 2000 groups of preset parameters).

In step 502, an optimized image sample set EI (e.g., including 2000 images, each of which is consistent with each image content in the OI, but is higher in quality) corresponding to the OI is obtained.

In step 503, a generator network part of a DCGAN is used.

In step 504, the generator network of the DCGAN is set to include N convolution layers, and an OI sample and an EI sample are input to the generator network in sequence to obtain outputs OIO and EIO of the $n^{th}$ layer, wherein n is more than or equal to 1 and less than or equal to N;

In step 505, the OIO and EIO obtained in step 504 are both set to be m matrixes, and the m matrixes are all vectorized and then are respectively combined into a matrix MO (corresponding to the OIO) and a matrix ME (corresponding to the EIO).

Figure 19:
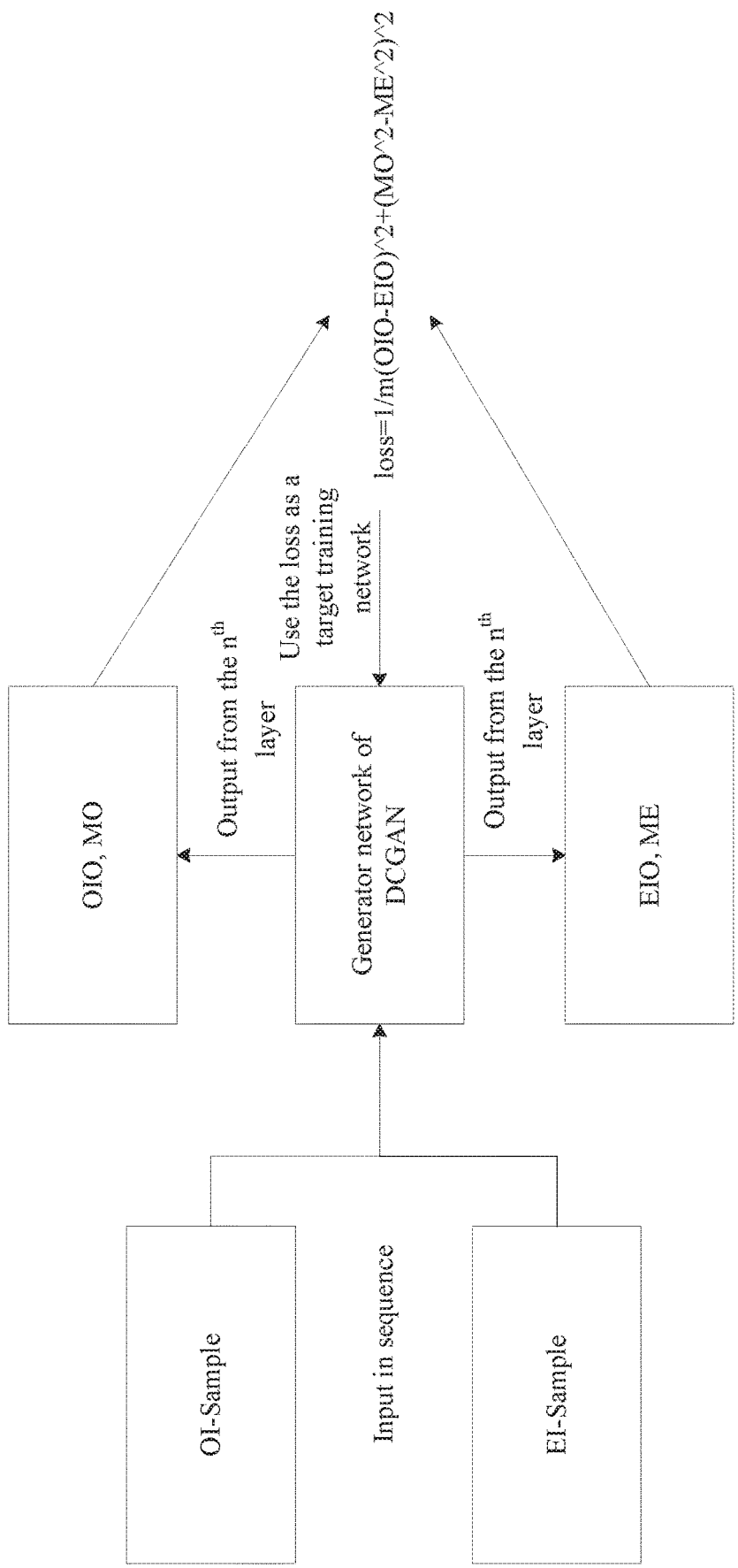
FIG. 19 is a schematic diagram of training a generator network of a DCGAN in Embodiment V of the present disclosure.

In step 506, the generator network of the DCGAN is trained by taking loss=1/m(OIO−EIO)^2+(MO^2−ME^2)^2 as an optimization target till the network is converged, as shown in FIG. 19, wherein loss is a loss function.

Figure 20:
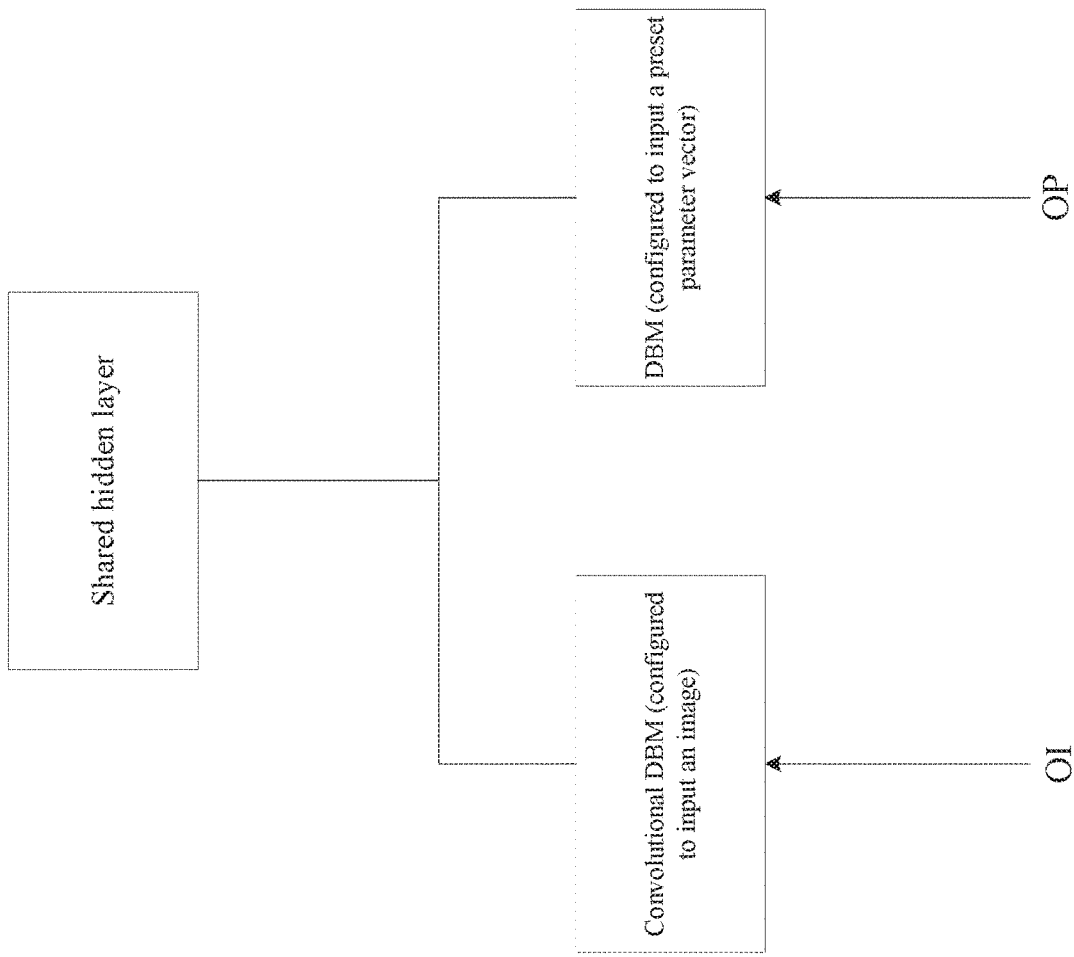
FIG. 20 is a schematic diagram of training a multi-mode DBM in Embodiment V of the present disclosure.

In step 507, a multi-mode DBM as shown in FIG. 20 is trained by using the OP and the OI till the Depth Boltzmann Machine (DBM) is converged, so as to obtain a trained multi-mode DBM.

The multi-mode DBM includes a convolutional DBM, a common DBM, and a shared hidden layer for connecting the convolutional DBM to the common DBM. The OI is input to the convolutional DBM, and the OP is input to the common DBM. The shared hidden layer establishes a connection between OI information and OP information.

An application stage can include steps as below.

Figure 21:
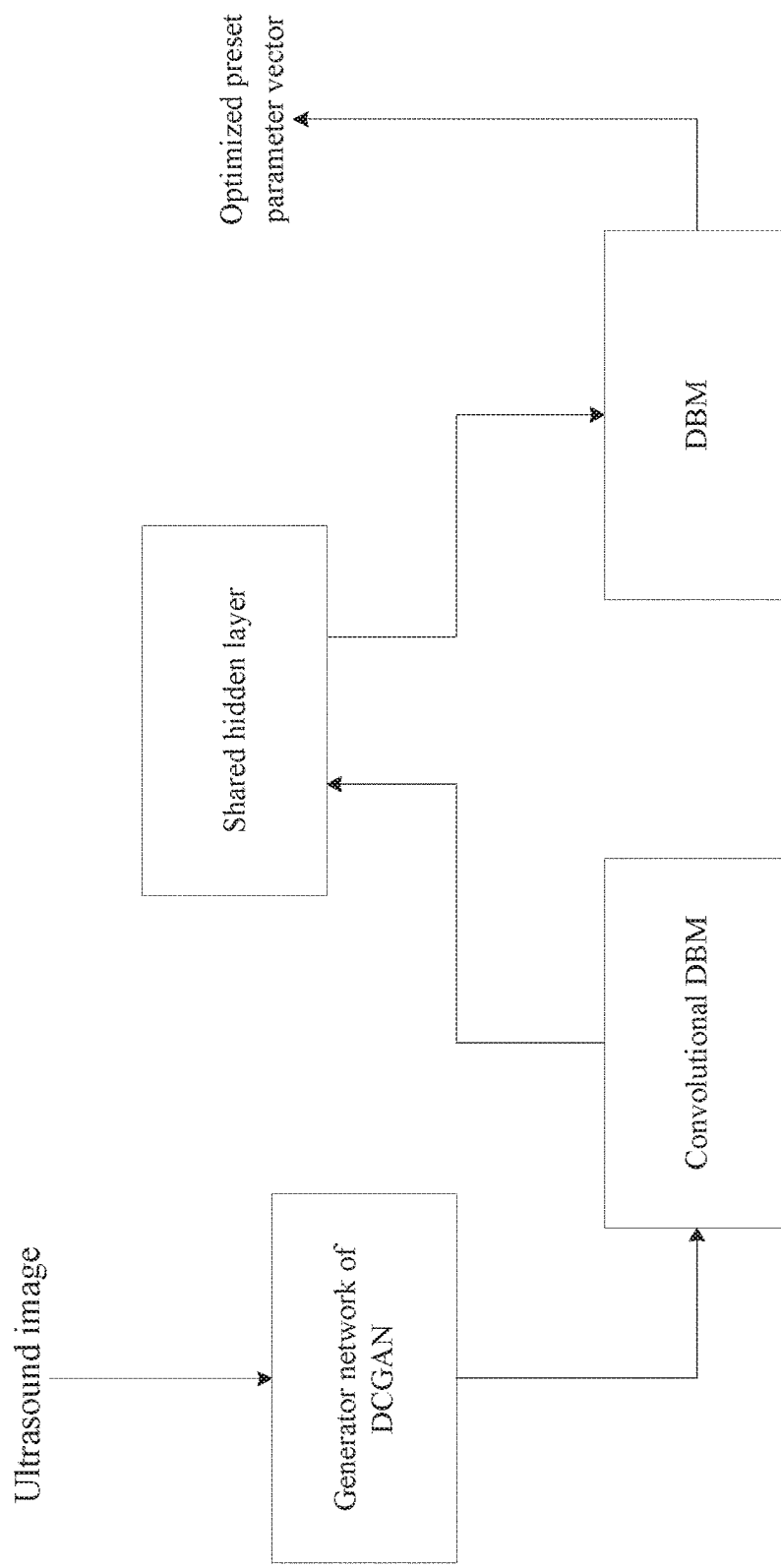
FIG. 21 is a schematic diagram of a combined neural network system in Embodiment V of the present disclosure.

In step a501, a neural network system as shown in FIG. 21 is formed by the generator network of the DCGAN and the multi-mode DBM, which are trained in step 506 and step 507 in the training stage.

The generator network of the DCGAN is connected with the convolution DBM in the multi-mode DBM.

In step a502, an ultrasound image is input to the generator network of the DCGAN in the neural network system as shown in FIG. 21. And at this moment, a vector obtained at the output end of the common DBM of the neural network system is an optimized parameter vector of the ultrasound imaging system (i.e., an optimized preset parameter vector).

Embodiment 6: this technical solution is specifically divided into a training stage and an application stage which are performed in sequence. Steps of each of the stages are as follows.

A training stage can include steps as below.

In step 601, presets of parameters of the ultrasound imaging system are randomly selected from an ultrasound apparatus, and one ultrasound image is acquired under the preset condition every time when one preset is selected. The ultrasound image is stored, and the preset parameter used by acquisition of the ultrasound image is recorded at the same time, so as to respectively obtain an image sample set OI (e.g., including 2000 images) and a preset parameter sample set OP (e.g., including 2000 groups of preset parameters).

In step 602, an optimized image sample set EI (e.g., including 2000 images, each of which is consistent with each image content in the OI, but is higher in quality) corresponding to the OI is obtained.

In step 603, a convolutional network part of a VGG network is used, wherein the VGG network is one of network structures of Deep Learning.

In step 604, the convolutional network of the VGG is set to include N layers, and an OI sample and an EI sample are input to the convolutional network in sequence to obtain outputs OIO and EIO of the $n^{th}$ layer, wherein n is more than or equal to 1 and less than or equal to N.

Figure 22:
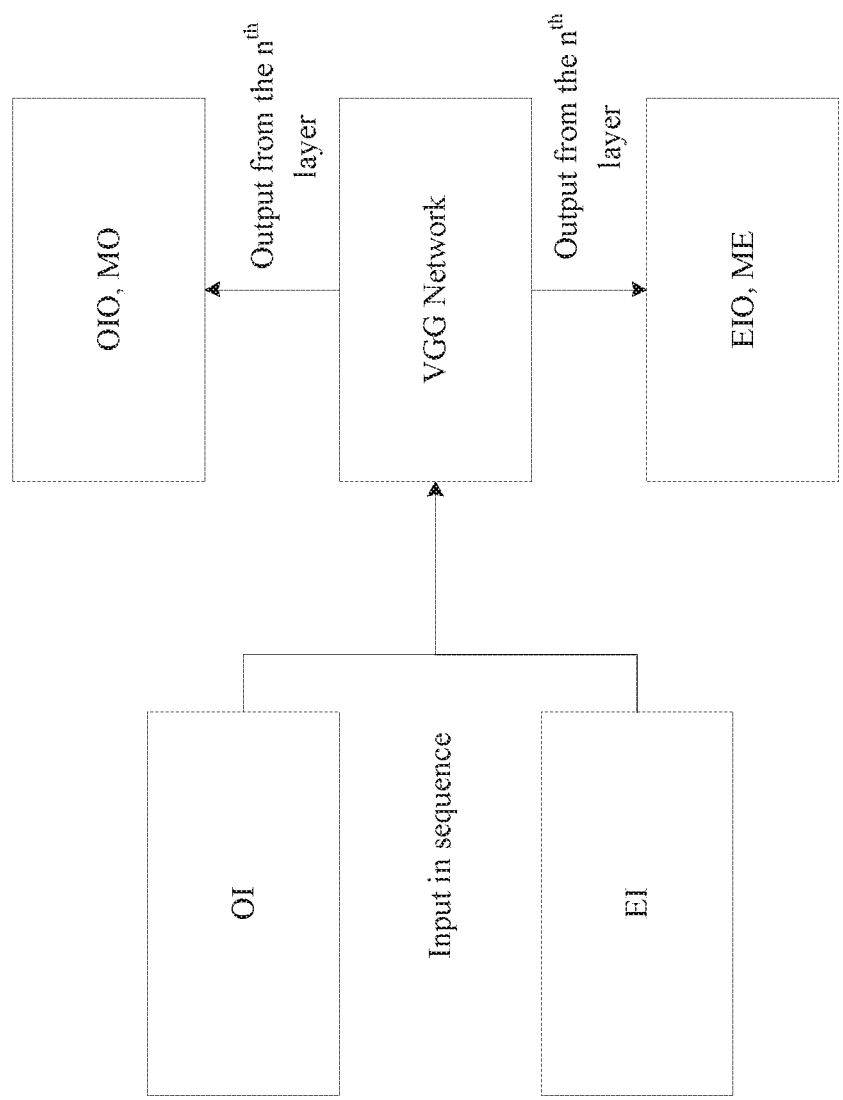
FIG. 22 is a schematic diagram of obtaining matrixes OIO, EIO, MO and ME in Embodiment VI of the present disclosure.
Figure 23:
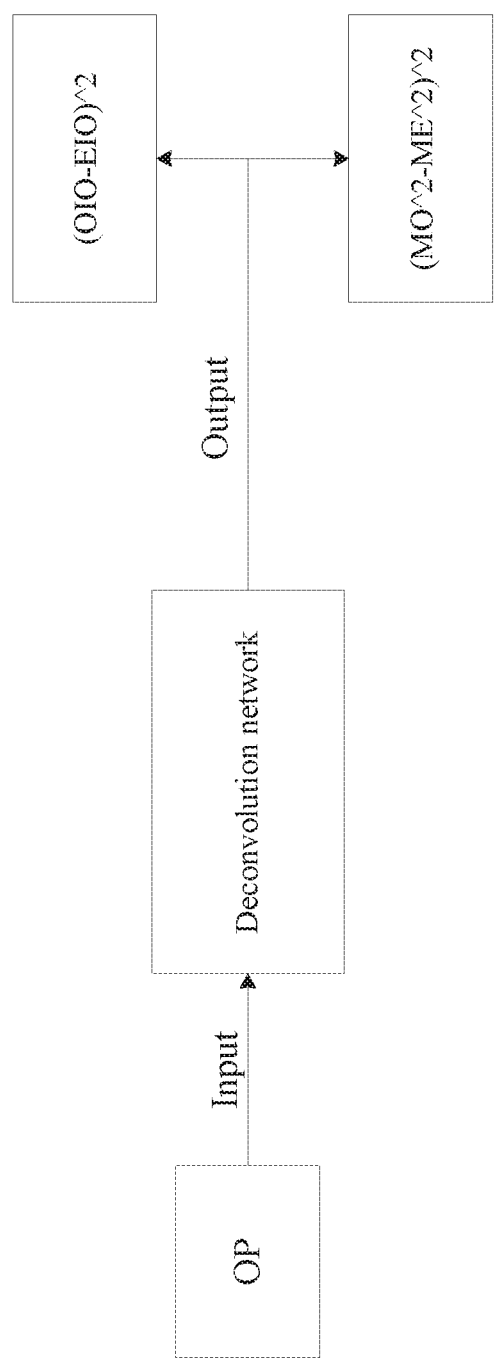
FIG. 23 is a schematic diagram of training a deconvolution network in Embodiment VI of the present disclosure.

In step 605, the OIO and EIO obtained in step 604 are both set to be m matrixes, and the m matrixes are all vectorized, and then the vectorized matrixes are arrayed in rows and are respectively combined into a matrix MO (corresponding to the OIO) and a matrix ME (corresponding to the EIO), as shown in FIG. 22;

In step 606, a deconvolution network is trained by taking the OP as an input and taking (OIO−EIO)^2 and (MO^2−ME^2)^2 as outputs, as shown in FIG. 23.

An application stage can include steps as below.

Figure 24:
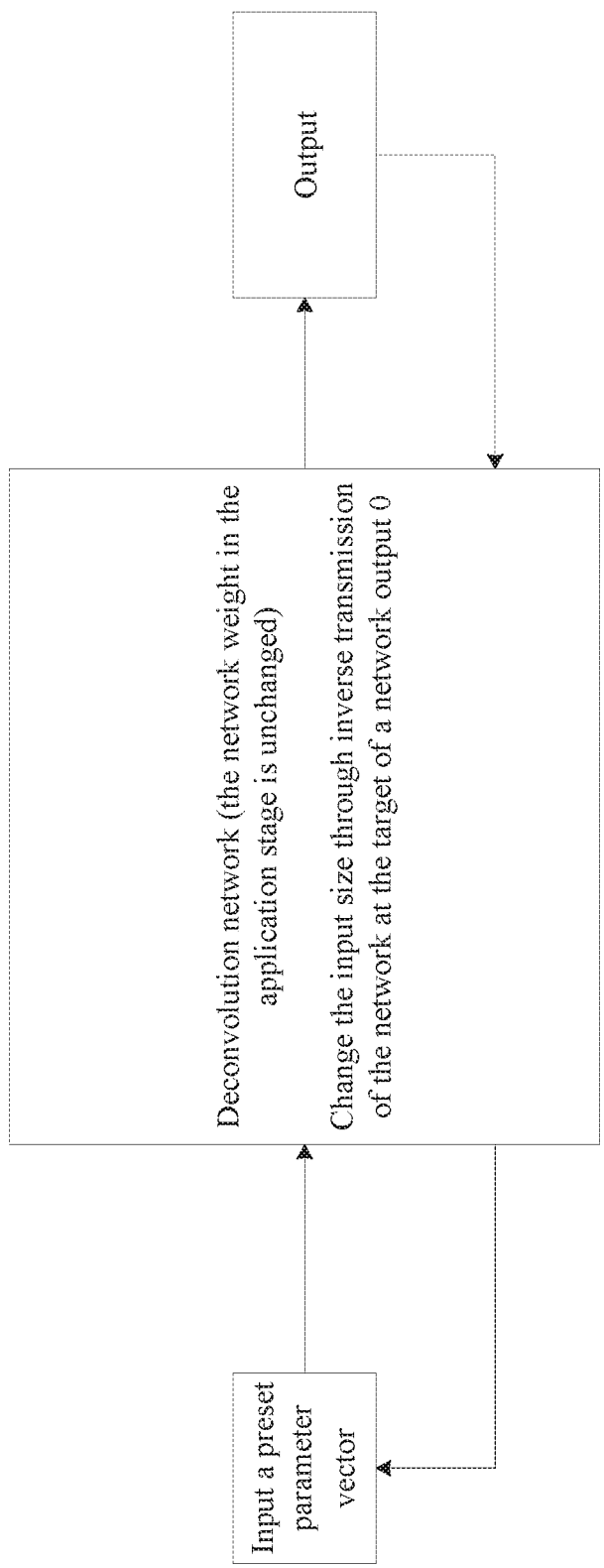
FIG. 24 is a schematic diagram of optimizing an input through a deconvolution network in Embodiment VI of the present disclosure.

In step a601, an ultrasound system preset parameter vector is input as an input to the deconvolution network trained in step 606. A preset parameter value of the network input end is optimized by keeping a network weight unchanged under the condition that a sum of the two outputs of the deconvolution network is 0 till the network is converged, wherein during the convergence, the modified preset parameter vector of the network input end is an optimized parameter vector of an ultrasound imaging system (i.e., an optimized preset parameter vector), and the process is as shown in FIG. 24.

Embodiment 7: this technical solution is specifically divided into a training stage and an application stage which are performed in sequence. Steps of each of the stages are as follows.

A training stage can include steps as below.

In step 701, presets of parameters of the ultrasound imaging system are randomly selected from an ultrasound apparatus, and one ultrasound image is acquired under the preset condition every time when one preset is selected. The ultrasound image is stored, and the preset parameter used by acquisition of the ultrasound image is recorded at the same time, so as to respectively obtain an image sample set OI (e.g., including 2000 images) and a preset parameter sample set OP (e.g., including 2000 groups of preset parameters).

In step 702, an optimized image sample set EI (e.g., including 2000 images, each of which is consistent with each image content in the OI, but is higher in quality) corresponding to the OI is obtained.

In step 703, a convolutional network part of a LeNet network is used, wherein the LeNet network is one of Deep Learning network structures.

Figure 25:
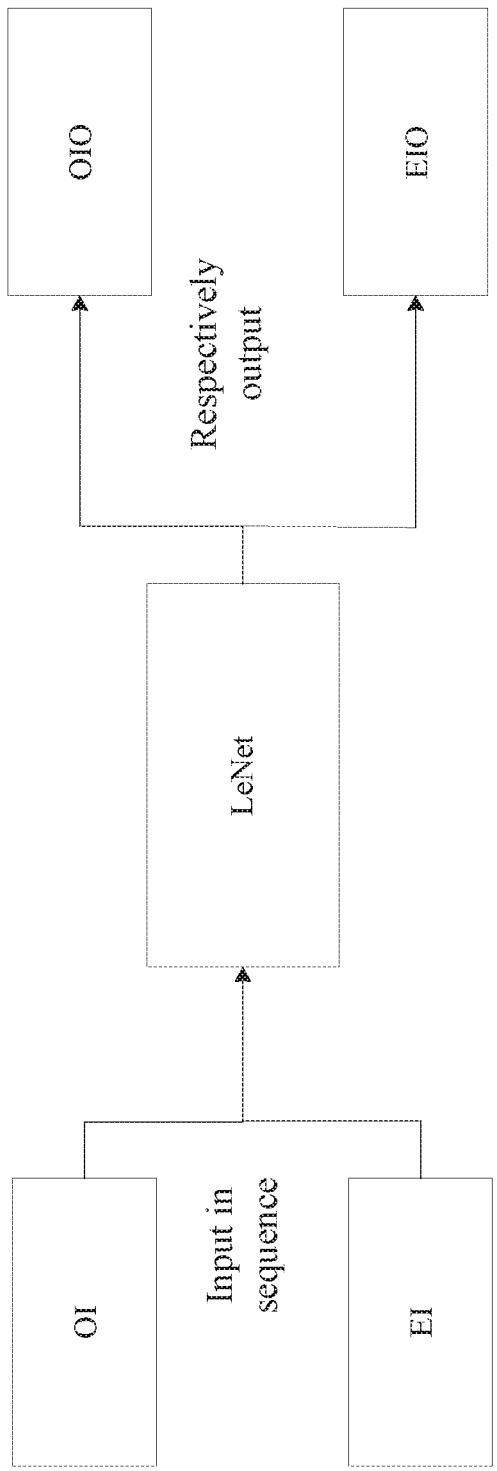
FIG. 25 is a schematic diagram of obtaining training data through LeNet in Embodiment VII of the present disclosure.

In step 704, an OI sample and an EI sample are input into the convolutional network of the LeNet in sequence to obtain outputs OIO and EIO of the last layer, wherein the obtained OIO and EIO are both m matrixes, as shown in FIG. 25.

Figure 26:
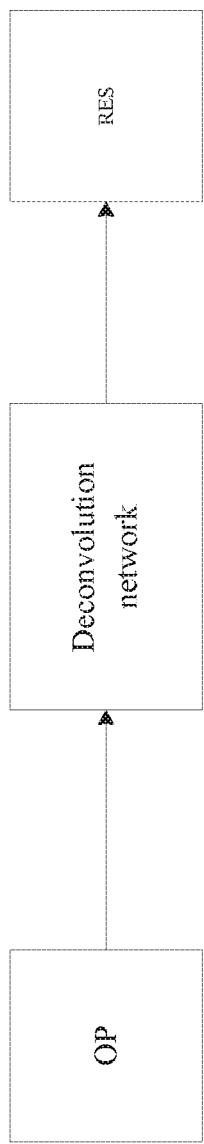
FIG. 26 is a schematic diagram of training a deconvolution network in Embodiment VII of the present disclosure.

In step 705, a deconvolution network is trained by using the OP as an input and using a corresponding res=OIO-EIO as an output, as shown in FIG. 26, wherein the res is a difference of the two matrixes OIO and EIO.

Figure 27:
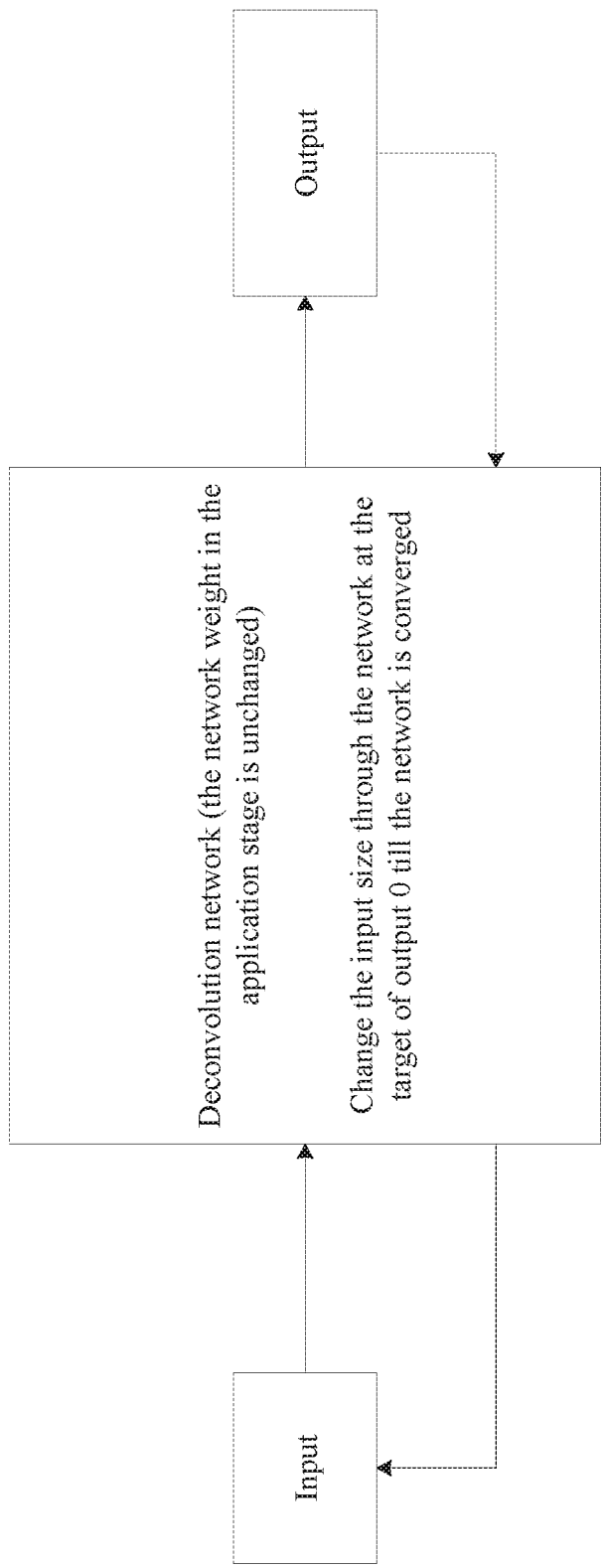
FIG. 27 is a schematic diagram of optimizing an input preset parameter through a deconvolution network in Embodiment VII of the present disclosure.

In an application stage, a preset parameter vector of an ultrasound system is input as an input to the deconvolution network trained in step 705. A preset parameter value of the network input end is optimized by keeping a network weight unchanged under the condition that the output of the deconvolution network is 0 till the network is converged. During the convergence, the modified preset parameter vector of the network input end is an optimized parameter vector of the ultrasound imaging system (i.e., an optimized preset parameter vector), and the process is as shown in FIG. 27.

At last, it should be noted that the above specific implementations are merely illustrative of the technical solutions of the present disclosure, and are not intended to be limiting. Although the present disclosure is described in detail with reference to the examples, it should be understood that those of ordinary skill in the art can make modifications or equivalent replacements to the technical solutions of the present disclosure without departing from the spirit and scope of the technical solutions of the present disclosure. These modifications and equivalent replacements shall fall within the scope of claims of the present disclosure.

What is claimed is:

1. A deep learning-based method for optimizing parameters of an ultrasound imaging system, comprising the following steps:

step 1: collecting samples for training a neural network, wherein the samples comprise ultrasound image samples I and corresponding parameter vector samples P of the ultrasound imaging system used by the ultrasound imaging system during collection of the ultrasound image samples;

step 2: building a neural network model, training a neural network by using the samples collected in step 1 till the neural network is converged, so as to obtain a trained neural network system "onn"; and step 3: inputting an original parameter vector p of the ultrasound imaging system or an original ultrasound image as an input into the neural network system "onn" trained in step 2, wherein at this moment, a parameter obtained from an output end of the "onn" is an optimized parameter vector of the ultrasound imaging system ep=onn(p), wherein the method specifically comprises:

a training stage:

step 101: randomly selecting presets of parameters of the ultrasound imaging system from an ultrasound apparatus, and acquiring one ultrasound image under the preset condition every time when one preset is selected; storing the ultrasound image, and recording the preset parameter used by the acquisition of the ultrasound image at the same time, so as to respectively obtain an image sample set OI and a preset parameter sample set OP;

step 102: obtaining an optimized image sample set EI corresponding to the OI;

step 103: training a Deep Convolutional Generation Adversarial Network (DCGAN) by using the OI and the EI till a generator network of the DCGAN outputs a corresponding optimized image under the condition of a specified original ultrasound image, so as to obtain a trained DCGAN, wherein the DCGAN comprises the generator network and a discriminator network; an OI sample is input into the generator network, and an image corresponding to the OI sample is generated through the generator network; then the discriminator network performs consistency comparison on the image generated by the generator network and a corresponding EI sample;

step 104: training a multi-mode Depth Boltzmann Machine (DBM) by using the OP and the OI till the DBM is converged, so as to obtain a trained multi-mode DBM, wherein the multi-mode DBM comprises a convolutional DBM, a common DBM, and a shared hidden layer for connecting the convolutional DBM to the common DBM; the OI is input to the convolutional DBM, and the OP is input to the common DBM; the shared hidden layer establishes a connection between OI information and OP information; and an application stage:

step a101, forming an artificial neural network system by the generator network part of the DCGAN trained in step 103 in the training stage and acquiring the multi-mode DBM trained in step 104 in the training stage, wherein an output end of the generator network is connected with the input end of the convolutional DBM; and step a102, inputting an original ultrasound image to the input end, namely an image input end, of the generator network, and outputting, by the parameter vector end of the common DBM, an optimized ultrasound imaging system parameter vector.

2. A deep learning-based method for optimizing parameters of an ultrasound imaging system, comprising the following steps:

step 1: collecting samples for training a neural network, wherein the samples comprise ultrasound image samples I and corresponding parameter vector samples P of the ultrasound imaging system used by the ultrasound imaging system during collection of the ultrasound image samples;

step 2: building a neural network model, training a neural network by using the samples collected in step 1 till the neural network is converged, so as to obtain a trained neural network system "onn"; and step 3: inputting an original parameter vector p of the ultrasound imaging system or an original ultrasound image as an input into the neural network system "onn" trained in step 2, wherein at this moment, a parameter obtained from an output end of the "onn" is an optimized parameter vector of the ultrasound imaging system ep=onn(p), wherein the method specifically comprises:

a training stage:

step 201: randomly selecting presets of the ultrasound imaging system parameters from the ultrasound apparatus, and acquiring one ultrasound image under the preset condition every time when one preset is selected; storing the ultrasound image, and recording the preset parameter used by the acquisition of the ultrasound image at the same time, so as to respectively obtain an image sample set OI and a preset parameter sample set OP;

step 202: obtaining an optimized image sample set EI corresponding to the OI;

step 203: training a multi-mode DBM by using the sample set OI and the sample set OP till the DBM is converged, so as to obtain a trained multi-mode DBM, wherein the multi-mode DBM comprises a convolutional DBM, a common DBM, and a shared hidden layer for connecting the convolutional DBM to the common DBM; the OI is input to the convolutional DBM, and the OP is input to the common DBM; the shared hidden layer establishes a connection between OI information and OP information;

step 204: inputting the sample set EI to the input end of the convolutional DBM of the trained multi-mode DBM in step 203, wherein at this moment, a result output by the multi-mode DBM from the preset parameter end, namely the parameter vector end of the common DBM, is a corresponding optimized preset parameter vector EP;

step 205: training a fully-connected neural network DNN by using the OP as an input and using the EP as an output; and an application stage:

step a201, inputting a preset parameter vector to the input end of the trained fully-connected neural network DNN obtained in step 205 in the training stage, wherein at this moment, a vector obtained at the output end is an optimized parameter vector of the ultrasound imaging system.

3. A deep learning-based method for optimizing parameters of an ultrasound imaging system, comprising the following steps:

step 1: collecting samples for training a neural network, wherein the samples comprise ultrasound image samples I and corresponding parameter vector samples P of the ultrasound imaging system used by the ultrasound imaging system during collection of the ultrasound image samples;

step 2: building a neural network model, training a neural network by using the samples collected in step 1 till the neural network is converged, so as to obtain a trained neural network system "onn"; and step 3: inputting an original parameter vector p of the ultrasound imaging system or an original ultrasound image as an input into the neural network system "onn" trained in step 2, wherein at this moment, a parameter obtained from an output end of the "onn" is an optimized parameter vector of the ultrasound imaging system ep=onn(p), wherein the method specifically comprises:

a training stage:

step 301: randomly selecting presets of parameters of the ultrasound imaging system from an ultrasound apparatus, and acquiring one ultrasound image under the preset condition every time when one preset is selected; storing the ultrasound image, and recording the preset parameter used by the acquisition of the ultrasound image at the same time, so as to respectively obtain an image sample set OI and a preset parameter sample set OP;

step 302: obtaining an optimized image sample set EI corresponding to the OI;

step 303: training a fully-connected automatic encoder DNN-AutoEncoder by using the preset parameter sample set OP, wherein the fully-connected automatic encoder comprises a fully-connected encoder and a fully-connected decoder, which are cascaded with each other; the fully-connected encoder is configured to compress high-dimension input information to a low-dimension space, and the fully-connected decoder is configured to convert the compressed low-dimension space information into the original high-dimension space;

step 304: training a convolution type automatic encoder CNN-AutoEncoder by using the image sample set OI, wherein the convolution-type automatic encoder comprises a convolution-type encoder and a convolution-type decoder, which are cascaded with each other; the convolution-type encoder is configured to compress high-dimension input information to a low-dimension space, and the convolution-type decoder is configured to convert the compressed low-dimension space information into the original high-dimension space;

step 305: inputting the OI into the convolution-type encoder of the CNN-AutoEncoder trained in step 304 to obtain an output MI, and inputting the OP into the fully-connected encoder of the DNN-AutoEncoder in step 303 to obtain an output MP; training a fully-connected neural network DNN-T by using the MI as an input and using the MP as an output;

step 306: forming a neural network system by the CNN-AutoEncoder convolution-type encoder part, the DNN-AutoEncoder fully-connected decoder part and the DNN-T,
wherein the CNN-AutoEncoder convolution-type encoder part is connected with the DNN-T, and the DNN-T is connected with the DNN-AutoEncoder fully-connected decoder part;
the sample set EI is input to the convolution-type encoder end of the neural network system CNN-AutoEncoder, and an optimized preset parameter sample set EP is obtained at the output end of the fully-connected decoder of the DNN-AutoEncoder of the neural network system;
step 307: training a fully-connected neural network DNN by using the preset parameter sample set OP obtained in step 301 and the optimized preset parameter sample set EP obtained in step 306 till the network is converged; and an application stage:
step a301: inputting a preset parameter vector to the DNN obtained in step 307 in the training stage, and obtaining an optimized parameter vector of the ultrasound imaging system at the output end.

4. A deep learning-based method for optimizing parameters of an ultrasound imaging system, comprising the following steps:
step 1: collecting samples for training a neural network, wherein the samples comprise ultrasound image samples I and corresponding parameter vector samples P of the ultrasound imaging system used by the ultrasound imaging system during collection of the ultrasound image samples;
step 2: building a neural network model, training a neural network by using the samples collected in step 1 till the neural network is converged, so as to obtain a trained neural network system "onn"; and
step 3: inputting an original parameter vector p of the ultrasound imaging system or an original ultrasound image as an input into the neural network system "onn" trained in step 2, wherein at this moment, a parameter obtained from an output end of the "onn" is an optimized parameter vector of the ultrasound imaging system ep=onn(p),
wherein the method specifically comprises:
a training stage:
step 401: randomly selecting presets of parameters of the ultrasound imaging system from an ultrasound apparatus, and acquiring one ultrasound image under the preset condition every time when one preset is selected; storing the ultrasound image, and recording the preset parameter used by the acquisition of the ultrasound image at the same time, so as to respectively obtain an image sample set OI and a preset parameter sample set OP;
step 402: obtaining an optimized image sample set EI corresponding to the OI;
step 403: training a DCGAN by using the sample sets OI and EI till a generator network of the DCGAN outputs a corresponding optimized image under the condition of inputting an original ultrasound image, so as to obtain a trained DCGAN,
wherein the DCGAN comprises a generator network and a discriminator network; an OI sample is input into the generator network, and an image corresponding to the OI sample is generated through the generator network; then the discriminator network performs consistency comparison on the image generated by the generator network and a corresponding EI sample;
step 404: training a fully-connected automatic encoder DNN-AutoEncoder by using the preset parameter sample set OP,
wherein the fully-connected automatic encoder comprises a fully-connected encoder and a fully-connected decoder which are cascaded with each other; the fully-connected encoder is configured to compress high-dimension input information to a low-dimension space, and the fully-connected decoder is configured to convert the compressed low-dimension space information into the original high-dimension space;
step 405: training a convolution-type automatic encoder CNN-AutoEncoder by using the image sample set OI,
wherein the convolution-type automatic encoder comprises a convolution-type encoder and a convolution-type decoder which are cascaded with each other; the convolution-type encoder is configured to compress high-dimension input information to a low-dimension space, and the convolution-type decoder is configured to convert the compressed low-dimension space information into the original high-dimension space;
step 406: inputting the OI into the convolution-type encoder of the CNN-AutoEncoder trained in step 405 to obtain an output MI, and inputting the OP into the fully-connected encoder of the DNN-AutoEncoder in step 404 to obtain an output MP; training the fully-connected neural network DNN-T by using the MI as an input and using the MP as an output; and an application stage:
step a401: forming a neural network system by the generator network of the DCGAN trained in step 403, the fully-connected decoder of the DNN-AutoEncoder trained in step 404 and the convolution-type encoder of the CNN-AutoEncoder trained in step 405,
wherein in the neural network system, the generator network of the DCGAN is connected with the convolution-type encoder of the CNN-AutoEncoder; the convolution-type encoder of the CNN-AutoEncoder is connected with the DNN-T; the DNN-T is connected with the fully-connected encoder of the DNN-AutoEncoder; and
step a402: inputting an original ultrasound image to the neural network system formed in step a401, and at this moment, an output of the neural network system is an optimized ultrasound imaging system parameter vector.

5. A deep learning-based method for optimizing parameters of an ultrasound imaging system, comprising the following steps:
step 1: collecting samples for training a neural network, wherein the samples comprise ultrasound image samples I and corresponding parameter vector samples P of the ultrasound imaging system used by the ultrasound imaging system during collection of the ultrasound image samples;
step 2: building a neural network model, training a neural network by using the samples collected in step 1 till the neural network is converged, so as to obtain a trained neural network system "onn"; and
step 3: inputting an original parameter vector p of the ultrasound imaging system or an original ultrasound image as an input into the neural network system "onn" trained in step 2, wherein at this moment, a parameter obtained from an output end of the "onn" is an optimized parameter vector of the ultrasound imaging system ep=onn(p), wherein the method specifically comprises:

a training stage:

step 501: randomly selecting presets of parameters of the ultrasound imaging system from an ultrasound apparatus, and acquiring one ultrasound image under the preset condition every time when one preset is selected; storing the ultrasound image, and recording the preset parameter used by the acquisition of the ultrasound image at the same time, so as to respectively obtain an image sample set OI and a preset parameter sample set OP;

step 502: obtaining an optimized image sample set EI corresponding to the OI;

step 503: using a generator network part of the DCGAN;

step 504: setting that the generator network of the DCGAN comprises N convolution layers, and inputting an OI sample and an EI sample to the generator network in sequence to obtain outputs OIO and EIO of the $n^{th}$ layer, wherein n is more than or equal to 1 and less than or equal to N;

step 505: setting that the OIO and EIO obtained in step 504 are both m matrixes, vectorizing all the m matrixes, and then respectively combining the matrixes into a matrix MO and a matrix ME;

step 506: training the generator network of the DCGAN by taking loss=$1/m(OIO-EIO)^2+(MO^2-ME^2)^2$ as an optimization target till the network is converged, wherein loss is a loss function;

step 507: training a multi-mode DBM by using the OP and the OI till the DBM is converged, so as to obtain a trained multi-mode DBM, wherein the multi-mode DBM comprises a convolutional DBM, a common DBM, and a shared hidden layer for connecting the convolutional DBM to the common DBM;

the OI is input to the convolutional DBM, and the OP is input to the common DBM; the shared hidden layer establishes a connection between OI information and OP information; and an application stage:

step a501: forming a neural network system by using the generator network of the DCGAN and the multi-mode DBM which are trained in step 506 and step 507 in the training stage, wherein in the neural network system, the generator network of the DCGAN is connected with the convolutional DBM in the multi-mode DBM; and step a502: inputting an ultrasound image to the generator network of the DCGAN in the neural network system, wherein at this moment, a vector obtained at the output end of the common DBM of the neural network system is an optimized parameter vector of the ultrasound imaging system.

6. A deep learning-based method for optimizing parameters of an ultrasound imaging system, comprising the following steps:

step 1: collecting samples for training a neural network, wherein the samples comprise ultrasound image samples I and corresponding parameter vector samples P of the ultrasound imaging system used by the ultrasound imaging system during collection of the ultrasound image samples;

step 2: building a neural network model, training a neural network by using the samples collected in step 1 till the neural network is converged, so as to obtain a trained neural network system "onn"; and step 3: inputting an original parameter vector p of the ultrasound imaging system or an original ultrasound image as an input into the neural network system "onn" trained in step 2, wherein at this moment, a parameter obtained from an output end of the "onn" is an optimized parameter vector of the ultrasound imaging system ep=onn(p), wherein the method specifically comprises:

a training stage:

step 601: randomly selecting presets of parameters of the ultrasound imaging system from ultrasound equipment, and acquiring one ultrasound image under the preset condition every time when one preset is selected; storing the ultrasound image, and recording the preset parameter used by the acquisition of the ultrasound image at the same time, so as to respectively obtain an image sample set OI and a preset parameter sample set OP;

step 602: obtaining an optimized image sample set EI corresponding to the OI;

step 603: using a convolutional network part of a VGG network;

step 604: setting that the convolutional network of the VGG comprises N layers, and inputting an OI sample and an EI sample to the convolutional network in sequence to obtain outputs OIO and EIO of the $n^{th}$ layer, wherein n is more than or equal to 1 and less than or equal to N;

step 605: setting that the OIO and EIO obtained in step 604 are both m matrixes, vectorizing all the m matrixes, and then arraying the vectorized matrixes in rows and respectively combining the matrixes into a matrix MO and a matrix ME;

step 606: training a deconvolution network by using the OP as an input and using $(OIO-EIO)^2$ and $(MO^2-ME^2)^2$ as outputs; and an application stage:

step a601: inputting a preset parameter vector of the ultrasound system as an input to the deconvolution network trained in step 606; and optimizing a preset parameter value of the network input end by keeping a network weight unchanged under the condition that a sum of the two outputs of the deconvolution network is 0 till the network is converged, wherein during the convergence, the modified preset parameter vector of the network input end is an optimized parameter vector of the ultrasound imaging system.

7. A deep learning-based method for optimizing parameters of an ultrasound imaging system, comprising the following steps:

step 1: collecting samples for training a neural network, wherein the samples comprise ultrasound image samples land corresponding parameter vector samples P of the ultrasound imaging system used by the ultrasound imaging system during collection of the ultrasound image samples;

step 2: building a neural network model, training a neural network by using the samples collected in step 1 till the neural network is converged, so as to obtain a trained neural network system "onn"; and step 3: inputting an original parameter vector p of the ultrasound imaging system or an original ultrasound image as an input into the neural network system "onn" trained in step 2, wherein at this moment, a parameter obtained from an output end of the "onn" is an optimized parameter vector of the ultrasound imaging system ep=onn(p), wherein the method specifically comprises:

a training stage:

step 701: randomly selecting presets of parameters of the ultrasound imaging system from an ultrasound apparatus, and acquiring one ultrasound image under the preset condition every time when one preset is selected; storing the ultrasound image, and recording the preset parameter used by the acquisition of the ultrasound image at the same time, so as to respectively obtain an image sample set OI and a preset parameter sample set OP;

step 702: obtaining an optimized image sample set EI corresponding to the OI;

step 703: using a convolutional network part of a LeNet network, wherein the LeNet network is one of Deep Learning network structures;

step 704: inputting an OI sample and an EI sample into the convolutional network of the LeNet, and obtaining outputs OIO and EIO of the last layer;

step 705: training a deconvolution network by using the OP as an input and using a correpsonding res=OIO-EIO as an output, wherein the res is a difference of the two matrixes OIO and EIO; and an application stage: inputting a preset parameter vector of the ultrasound system as an input into the deconvolution network trained in step 705; and optimizing a preset parameter value of the network input end by keeping a network weight unchanged under the condition that the output of the deconvolution network is 0 till the network is converged, wherein during the convergence, the modified parameter vector of the network input end is an optimized parameter vector of the ultrasound imaging system.

\* \* \* \* \*

UNITED STATES PATENT AND TRADEMARK OFFICE
CERTIFICATE OF CORRECTION

PATENT NO. : 11,564,661 B2
APPLICATION NO. : 16/766643
DATED : January 31, 2023
INVENTOR(S) : Zhiwei Zhang et al.

It is certified that error appears in the above-identified patent and that said Letters Patent is hereby corrected as shown below:

In the Claims

Claim 7 Column 16, Line 53, "samples 1and" should read --samples I and--.

Signed and Sealed this
Twenty-ninth Day of August, 2023

Katherine Kelly Vidal
*Director of the United States Patent and Trademark Office*